(12) United States Patent
Traxler et al.

(10) Patent No.: US 6,180,636 B1
(45) Date of Patent: Jan. 30, 2001

(54) SUBSTITUTED PYRROLOPYRIMIDINES AND PROCESSES FOR THEIR PREPARATION

(75) Inventors: Peter Traxler, Schönenbuch; Guido Bold, Gipf-Oberfrick, both of (CH); Marc Lang, Mulhouse (FR); Jörg Frei, Hölstein (CH)

(73) Assignee: Novartis AG, Basel (CH)

(*) Notice: Under 35 U.S.C. 154(b), the term of this patent shall be extended for 0 days.

(21) Appl. No.: 09/242,592

(22) PCT Filed: Aug. 21, 1997

(86) PCT No.: PCT/EP97/04564

§ 371 Date: Feb. 19, 1999

§ 102(e) Date: Feb. 19, 1999

(87) PCT Pub. No.: WO98/07726

PCT Pub. Date: Feb. 26, 1998

(30) Foreign Application Priority Data

Aug. 23, 1996 (CH) .................................................. 2071/96

(51) Int. Cl.[7] ..................... A61K 31/519; C07D 487/04; A61P 35/00
(52) U.S. Cl. ............................................. 514/258; 544/280
(58) Field of Search .............................. 544/280; 214/258

(56) References Cited

U.S. PATENT DOCUMENTS

| 5,654,307 | * | 8/1997 | Bridges et al. | 514/258 |
| 5,661,148 | * | 8/1997 | Sakuma et al. | 514/218 |
| 5,686,457 |  | 11/1997 | Traxler et al. | 514/258 |

FOREIGN PATENT DOCUMENTS

| 3036930 | 5/1982 | (DE) . |
| 682 027 | 11/1995 | (EP) . |
| 773023 | 5/1997 | (EP) . |
| 795556 | 9/1997 | (EP) . |
| WO 92/20642 | 11/1992 | (WO) . |
| WO 95 19774 | 7/1995 | (WO) . |
| WO 95/19970 | 7/1995 | (WO) . |
| WO 96/10028 | 4/1996 | (WO) . |
| WO 96/31510 | 10/1996 | (WO) . |
| WO 96/40142 | 12/1996 | (WO) . |
| WO 97/02266 | 1/1997 | (WO) . |
| WO 97/27199 | 7/1997 | (WO) . |
| WO 98/14449 | 4/1998 | (WO) . |
| WO 98/14450 | 4/1998 | (WO) . |

OTHER PUBLICATIONS

Lydon et al. (Int. J. Cancer: 76, 154–163 (1998).*
WPIDS Abstract 1997–502726.
Girgis N.S. et al., Liebigs Ann.Chem., pp. 2066–2072 (1983).
Jorgensen A. et al., Liebigs Ann.Chem., pp. 142–148 (1985).
Jorgensen A. et al., J. Heterocyclic Chem., vol. 22, pp. 859–863, (1985).
Derwent Abstract No. 92–213005/26 (1992).
Dow R.L. et al., 209th ACS–meeting Apr. 2nd to 7th, Anaheim, Calif. (1995).
Sun L. et al., 209th ACS–meeting Apr. 2nd to 7th, Anaheim, Calif. (1995).
Bridges A.J. et al., 86th Annual Meeting, American Association of Cancer Res., Toronto, Canada, (Mar. 18–22, 1995).
J.P.Marquet et al., Chimie Therapeutique, pp. 427–438 (1971) (incl. CAPLUS Abstract 1972:126924).
Mattson R.J. et al., Synthesis, pp. 217–218 (1979).

* cited by examiner

*Primary Examiner*—Bruck Kifle
(74) *Attorney, Agent, or Firm*—Joseph J. Borovian

(57) ABSTRACT

There are described 7H-pyrrolo[2,3-d]pyrimidine derivatives of the formula I

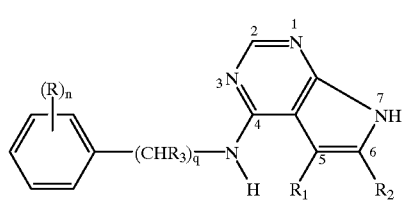

in which the substituents are as defined in claim 1.

These compounds inhibit the tyrosine kinase activity of the receptor for the epidermal growth factor (EGF) and c-erbB2 kinase and can be used as anti-tumor agents.

8 Claims, No Drawings

SUBSTITUTED PYRROLOPYRIMIDINES AND PROCESSES FOR THEIR PREPARATION

The invention relates to 7H-pyrrolo[2,3-d]pyrimidine derivatives and to processes and novel intermediates for their preparation, to pharmaceutical formulations comprising such derivatives and to the use of these derivatives as medicaments.

The invention relates to 7H-pyrrolo[2,3-d]pyrimidine derivatives of the formula I

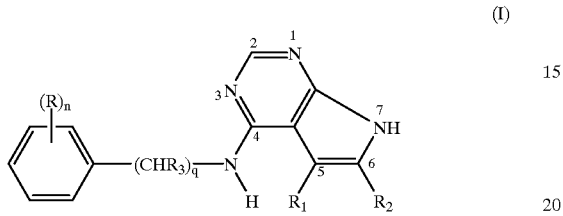

in which n is 0 to 3,
q is 0 or 1,
R is halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, it being possible, if two or more radicals R are present in the molecule, for these to be identical to or different from one another,
one of the radicals $R_1$ and $R_2$ is hydrogen or lower alkyl, and the other of the radicals $R_1$ and $R_2$ is
a) a radical of the formula II

in which u is 1 to 3 and
at least one radical $R_4$ is amidino, guanidino, ureido, $N^3$-lower alkylureido, $N^3,N^3$-di-lower alkylureido, $N^3$-phenylureido, $N^3,N^3$-diphenylureido, thiocarbamoyl, thioureido, $N^3$-lower alkylthioureido, $N^3,N^3$-di-lower alkylthioureido, lower alkoxycarbonylamino, benzyloxycarbonylamino, morpholine-4-carbonyl, piperazine-1-carbonyl, 4-lower alkylpiperazine-1-carbonyl, lower alkylsulfonylamino, benzenesulfonylamino, toluenesulfonylamino, thiophene-2-carbonylamino, furan-2-carbonylamino, benzylamino, hydroxymethyl, aminomethyl or a radical of the formula $-N=C(R_5)-R_6$, in which $R_5$ is hydrogen or lower alkyl and $R_6$ is di-lower alkylamino, piperidino, 4-lower alkylpiperazino or morpholino, and the other radical(s) $R_4$ is (are) halogen, lower alkyl, hydroxyl, lower alkanoyloxy, lower alkoxy, carboxyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, it being possible, if two or more radicals $R_4$ are present in the molecule, for these to be identical to or different from one another, or is b) a radical of the formula III

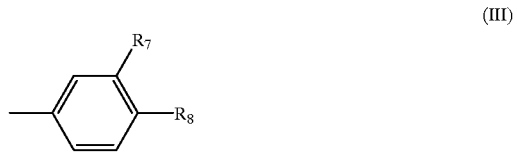

in which $R_7$ is lower alkoxy or benzyloxy and $R_8$ is hydroxyl or benzyloxy, or is c) amino-lower alkyl, in which the amino group is substituted by one or two hydroxy-lower alkyl, amino-lower alkyl, carboxy-lower alkyl, lower alkoxycarbonyl-lower alkyl, benzyloxycarbonyl-lower alkyl or benzyl radicals, which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or is d) piperidine-1-carbonyl, piperazine-1-carbonyl, 4-lower alkylpiperazine-1-carbonyl, morpholine-4-carbonyl, thiocarbamoyl, a heterocyclic radical bonded via a ring carbon atom and having five ring members and 1–4 ring heteroatoms, selected from oxygen, nitrogen and sulfur, or is e) 4-lower alkylpiperazinomethyl or a lower alkyl radical which is substituted by a heterocyclic radical other than piperazinyl and having five or six ring members and 1–4 ring heteroatoms, selected from oxygen, nitrogen and sulfur, or is f) a radical of the formula $-CH=N-OR_9$ in which $R_9$ is hydrogen or lower alkyl, or g) if q is 1, additionally to the definitions given above in the sections a) to f) can also be phenyl which is substituted by halogen, lower alkyl, trifluoromethyl or lower alkoxy, and $R_3$ is hydrogen, lower alkyl, lower alkoxycarbonyl, carbamoyl, N-lower alkylcarbamoyl or N,N-di-lower alkylcarbamoyl, and their salts.

The prefix "lower" used hereinbefore and hereinafter denotes a radical having up to and including a maximum of 7, especially up to and including a maximum of 4, and in particular having 1 or 2, carbon atoms.

Preferably, n is 0 or especially 1. When there is only one substituent R, this substituent is preferably in the 3-position on the phenyl ring. When two substituents R are present, these substituents are preferably in the 3- and 4-positions.

Halogen R is bromine, iodine or preferably fluorine or chlorine. When n is 1, R is preferably chlorine.

Lower alkyl is, for example, methyl.

Lower alkanoyloxy is, for example, acetoxy.

Lower alkoxy is, for example, methoxy.

Lower alkanoyl is, for example, acetyl.

Lower alkoxycarbonyl is, for example, methoxycarbonyl.

N-Lower alkylcarbamoyl is, for example, N-methylcarbamoyl, N-(n-butyl)carbamoyl or N-(3-methylbut-1-yl)carbamoyl. N,N-Di-lower alkylcarbamoyl is, for example, N,N-di-methylcarbamoyl.

Lower alkanoylamino is, for example, acetylamino.

Lower alkylamino is, for example, methylamino.

N,N-Di-lower alkylamino is, for example, dimethylamino.

Lower alkoxycarbonylmethoxy is, for example, methoxycarbonylmethoxy.

The radical $R_1$ is preferably hydrogen.

The symbol u is preferably 1. In this case, the radical $R_4$ is preferably in the 3- or 4-position of the phenyl ring.

Amidino is a radical of the formula —C(=NH)—$NH_2$.

Guanidino is a radical of the formula —NH—C(=NH)—$NH_2$.

Ureido is a radical of the formula —NH—C(=O)—$NH_2$.

$N^3$-Lower alkyl ureido is a radical of the formula —NH—C(=O)—NH-lower alkyl, preferably $N^3$-ethylureido.

$N^3$, $N^3$-Di-lower alkylureido is a radical of the formula —NH—C(=O)—N(lower alkyl)$_2$.

$N^3$-Phenylureido is a radical of the formula —NH—C(=O)—NH-phenyl.

$N^3$, $N^3$-Diphenylureido is a radical of the formula —NH—C(=O)—N(phenyl)$_2$.

Thioureido is a radical of the formula —NH—C(=S)—$NH_2$.

$N^3$-Lower alkylthioureido is a radical of the formula —NH—C(=S)—NH-lower alkyl, preferably $N^3$-methylthioureido.

$N^3$,$N^3$-Di-lower alkylthioureido is a radical of the formula —NH—C(=S)—N(lower alkyl)$_2$.

Lower alkoxycarbonylamino is, for example, methoxycarbonylamino, ethoxycarbonylamino, isopropyloxycarbonylamino or 2-methylpropyloxycarbonylamino.

Morpholine-4-carbonyl is also called morpholinocarbonyl.

4-Lower alkylpiperazine-1-carbonyl is preferably 4-methylpiperazine-1-carbonyl.

Lower alkylsulfonylamino is preferably methylsulfonylamino, ethylsulfonylamino or isopropylsulfonylamino.

The radical of the formula —N=C($R_5$)—$R_6$, in which $R_5$ is hydrogen and $R_6$ is di-lower alkylamino, is called di-lower alkylaminomethylenamino. Corresponding radicals in which $R_6$ is piperidino, 4-lower alkylpiperazino or morpholino are called $R_6$-methylenamino radicals, in which $R_6$ is defined as above, e.g. as piperidinomethylamino.

$R_5$ is preferably hydrogen.

Di-lower alkylamino $R_6$ is preferably dimethylamino or diethylamino.

4-Lower alkylpiperazino is 4-lower alkylpiperazin-1-yl, preferably 4-methylpiperazin-1-yl.

Morpholino is 4-morphotinyl.

Lower alkoxy $R_7$ is preferably methoxy.

Amino-lower alkyl $R_1$ or $R_2$ in which the amino group is substituted by one or two hydroxy-lower alkyl, amino-lower alkyl, carboxy-lower alkyl, lower alkoxycarbonyl-lower alkyl, benzyloxycarbonyl-lower alkyl or benzyl radicals which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, is preferably appropriately substituted aminomethyl.

Amino-lower alkyl $R_1$ or $R_2$ in which the amino group is substituted by one or two hydroxy-lower alkyl radicals is preferably, for example, a radical of the formula —$CH_2$—NH($CH_2$—$CH_2$)$_2$.

Amino-lower alkyl $R_1$ or $R_2$ in which the amino group is substituted by one or two benzyl radicals which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, is preferably, for example, a radical of the formula —$CH_2$—NH—$CH_2$—$C_6H_4$—$OCH_3$, such as, in particular, 4-methoxyphenylmethylaminomethyl, or 4-hydroxyphenylmethylaminomethyl.

Thiocarbamoyl is the radical of the formula —C(=S)—$NH_2$ and is also called aminothiocarbonyl.

A heterocyclic radical $R_1$ or $R_2$ bonded via a ring carbon atom and having five ring members and 1–4 ring heteroatoms, selected from oxygen, nitrogen and sulfur, is unsubstituted or substituted, e.g. pyrrolyl, thienyl, furyl or preferably tetrazol-5-yl which is unsubstituted or substituted by lower alkyl, or thiazol-2-yl which is unsubstituted or substituted by lower alkoxyphenyl, e.g. thiazol-2-yl, 4-(4-methoxyphenyl)thiazol-2-yl, 4-ethylthiazol-2-yl or 4,5-dimethylthiazol-2-yl.

Tetrazol-5-yl is 1H-tetrazol-5-yl or the tautomeric 2H-tetrazol-5-yl or a mixture of these two tautomeric forms.

Tetrazol-5-yl substituted by lower alkyl is $N^1$-lower alkyltetrazol-5-yl or $N^2$-lower alkyltetrazol-5-yl, in particular 1-methyltetrazol-5-yl or 2-methyltetrazol-5-yl.

A heterocyclic radical other than piperazinyl and having five or six ring members and 1–4 ring heteroatoms, selected from oxygen, nitrogen and sulfur, is such an unsubstituted or substituted radical, e.g. pyrrolyl, thienyl, furyl, tetrazol-5-yl which is unsubstituted or substituted by lower alkyl; thiazol-2-yl which is unsubstituted or substituted by lower alkoxyphenyl, or morpholino or 4-lower alkylpiperazin-1-yl.

Lower alkyl $R_1$ or $R_2$ which is substituted by such a heterocyclic radical is preferably appropriately substituted methyl, preferably 4-methylpiperazin-1-ylmethyl or morpholinomethyl.

The radical —CH=N—$OR_9$ $R_1$ or $R_2$ can be present in the trans- or cis-configuration.

Phenyl $R_1$ or $R_2$ which is substituted by halogen, lower alkyl, trifluoromethyl or lower alkoxy is, for example, 4-methoxyphenyl. $R_1$ or $R_2$ can only be phenyl which is substituted in this way if in formula I the symbol q is 1.

$R_3$ is preferably methyl.

Salts of compounds of the formula I are especially acid addition salts with organic or inorganic acids, especially the pharmaceutically acceptable, non-toxic salts. Suitable inorganic acids are, for example, carbonic acid (preferably in the form of carbonates or hydrogencarbonates); hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcystine, pyruvic acid, acetoacetic acid, phosphoserine, 2- or 3-glycerophosphoric acid, glucose-6-phosphoric acid, glucose-1-phosphoric acid, fructose- 1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

Compounds of the formula I having at least one acid group, for example a free carboxyl group, are capable of forming internal salts or metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethylpiperidine or N,N'-dimethylpiperazine.

For isolation or purification purposes it is also possible to use pharmaceutically unsuitable salts, for example picrates or perchlorates. Only salts that are pharmaceutically acceptable and non-toxic (at the appropriate doses) are used therapeutically and these salts are therefore preferred.

In view of the close relationship between the novel compounds in free form and in the form of their salts, including those salts that can be used as intermediates, for example in the purification or identification of the novel compounds, hereinbefore and hereinafter the free compounds are to be understood as meaning also the corresponding salts, as appropriate and expedient.

The compounds of the formula I have valuable pharmacologically useful properties. In particular they display specific inhibitory activities that are of pharmacological interest. They are effective primarily as protein tyrosine kinase inhibitors and/or (furthermore) as inhibitors of protein serine/threonine kinases; they exhibit, for example, potent inhibition of the tyrosine kinase activity of the receptor for the epidermal growth factor (EGF) and of c-erbB2 kinase. These receptor-specific enzyme activities play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase (EGF-R-PTK) is a prerequisite for cell division and thus for the proliferation of the cell population. An increase in the number of EGF-receptor-specific tyrosine kinase inhibitors thus inhibits the proliferation of the cells. The same applies analogously to the other protein kinases mentioned hereinbefore and hereinafter.

In addition to or instead of inhibiting EGF receptor protein tyrosine kinase, the compounds of the formula I also inhibit to varying extents other protein tyrosine kinases that are involved in signal transmission mediated by trophic factors, for example abl kinase, especially v-abl kinase, kinases from the family of the src kinases, especially c-src kinase, lck, fyn; other kinases of the EGF family, for example c-erbB2 kinase (HER-2), c-erbB3 kinase, c-erbB4 kinase; members of the family of the PDGF receptor protein tyrosine kinases, for example PDGF receptor kinase, CSF-1 receptor kinase, Kit receptor kinase, VEGF receptor kinase and FGF receptor kinase; the receptor kinase of the insulin-like growth factor (IGF-1 kinase), and serine/threonine kinases, for example protein kinase C or cdc kinases, all of which play a part in growth regulation and transformation in mammalian cells, including human cells.

The inhibition of EGF-receptor-specific protein tyrosine kinase (EGF-R-PTK) can be demonstrated using known methods, for example using the recombinant intracellular domain of the EGF receptor (EGF-R ICD; see, for example, E. McGlynn et al., Europ. J. Biochem. 207, 265–275 (1992)). Compared with the control without inhibitor, the compounds of the formula I inhibit the enzyme activity by 50% ($IC_{50}$), for example in a concentration of from 0.0005 to 1 $\mu$M, especially from 0.001 to 0.1 $\mu$M.

The action of the compounds of the formula I on EGF-stimulated cellular tyrosine phosphorylation in the EGF-receptor can be determined in the human A431 epithelial carcinoma cell line by means of an ELISA which is described in U. Trinks et al., J. Med. Chem. 37:7, 1015–1027 (1994). In this test (EGFR-ELISA) the compounds of the formula I exhibit an $IC_{50}$ of approximately 0.001 to 1 $\mu$M.

Stimulation of quiescent BALB/c3T3 cells with EGF rapidly induces the expression of c-fos mRNA. Pretreatment of the cells with a compound of the formula I before the stimulation with EGF inhibits c-fos expression at an $IC_{50}$ of approximately from 0.001 to 0.1 $\mu$M. This test procedure is likewise described in U. Trinks et al., J. Med. Chem. 37:7,1015–1027 (1994).

In the micromolar range too, the compounds of the formula I also exhibit, for example, inhibition of the cell growth of EGF-dependent cell lines, for example the epidermoid BALB/c mouse keratinocyte cell line (see Weissmann, B. A., and Aaronson, S. A., Cell 32, 599 (1983)) or the A431 cell line, which are recognized as useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)), the inhibitory activity of the compounds of the formula I is determined, briefly, as follows: BALB/MK cells (10 000/microtiter plate well) are transferred to 96-well microtiter plates. The test compounds (dissolved in DMSO) are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the MK cells is measured by means of Methylene Blue staining: after the incubation the cells are fixed with glutaraldehyde, washed with water and stained with 0.05% Methylene Blue. After a washing step the stain is eluted with 3% HCl and the optical density per well of the microtiter plate is measured using a Titertek Multiscan at 665 nm. $IC_{50}$ values are determined by a computer-aided system using the formula:

$$IC_{50}=[(OD_{test}-OD_{start})/(OD_{control}-OD_{start})]\times 100.$$

The $IC_{50}$ value in these experiments is given as that concentration of the test compound in question that results in a cell count that is 50% lower than that obtained using the control without inhibitor. The compounds of the formula I display inhibitory activity in the micromolar range, for example an $IC_{50}$ of approximately from 0.1 to 1 $\mu$M.

The compounds of the formula I display inhibition of the growth of tumor cells also in vivo, as shown, for example, by the test described below: the test is based on inhibition of the growth of the human epidermoid carcinoma A431 (ATCC No. CRL 1555; American Type Culture Collection, Rockville, Md., USA; see Santon, J. B., et al., Cancer Research 46, 4701–4705 (1986) and Ozawa, S., et al., Int. J. Cancer 40, 706–710 (1987)), which is transplanted into female BALB/c nude mice (Bomholtgard, Denmark). This carcinoma exhibits a growth that correlates with the extent of the expression of the EGF-receptor. In the experiment, tumors having a volume of approximately 1 cm$^3$ cultured in vivo are surgically removed from experimental animals under sterile conditions. These tumors are comminuted and suspended in 10 volumes (w/v) of phosphate-buffered saline. The suspension is injected s.c. (0.2 ml/mouse in phosphate-buffered saline) into the left flank of the animals. Alternatively, 1×10$^6$ cells from an in vitro culture in 0.2 ml of phosphate-buffered saline can be injected. Treatment with test compounds of the formula I is started 5 or 7 days after transplantation, when the tumors have reached a diameter of 4–5 mm. The active compound in question is administered (in different doses for different animal groups) once a day for 15 successive days. The tumor growth is determined by measuring the diameter of the tumors along three axes that are perpendicular to each other. The tumor volumes are calculated using the known formula p×L×D$^2$/6 (see Evans, B. D., et al., Brit. J. Cancer 45, 466–8 (1982)). The results are given as treatment/control percentages (T/C×100=T/C %). At a dose of from 3 to 50 mg/kg of active ingredient, distinct inhibition of the tumor growth is found, for example T/C % values of less than 10, which indicates strong inhibition of tumor growth.

As well as or instead of inhibiting EGF-receptor protein tyrosine kinase, the compounds of the formula I also inhibit other protein tyrosine kinases that are involved in signal transmission mediated by trophic factors, for example abl kinase, such as especially v-abl kinase (IC$_{50}$ for example from 0.01 to 5 µM), kinases from the family of the src kinases, such as especially c-src kinase (IC$_{50}$ for example from 0.1 to 10 µM) and c-erbB2 kinase (HER-2), and serine/threonine kinases, for example protein kinase C, all of which are involved in growth regulation and transformation in mammalian cells, including human cells.

The abovementioned inhibition of v-abl tyrosine kinase is determined by the methods of N. Lydon et al., Oncogene Research 5, 161–173 (1990) and J. F. Geissler et al., Cancer Research 52, 4492–4498 (1992). In these methods [Val$^5$]-angiotensin II and [-γ-$^{32}$P]-ATP are used as substrates.

The inhibition of c-erbB2 tyrosine kinase (HER-2) can be determined, for example, analogously to the method used for EGF-R-TPK (see C. House et al., Europ. J. Biochem 140, 363–367 (1984)). The c-erbB2 kinase can be isolated, and its activity determined, by means of protocols known per se, for example in accordance with T. Akiyama et al., Science 232, 1644 (1986).

The compounds of the formula I which inhibit the tyrosine kinase activity of the receptor for the epidermal growth factor (EGF) or furthermore of the other protein tyrosine kinases mentioned are therefore useful, for example, in the treatment of benign or malignant tumors. They are capable of effecting tumor regression and of preventing the formation of tumor metastases and the growth of micrometastases. They can be used especially in the case of epidermal hyperproliferation (psoriasis), in the treatment of neoplasias of epithelial character, e.g. mammary carcinomas, and in leukemias. In addition, the compounds of the formula I (especially the novel compounds) can be used in the treatment of those disorders of the immune system in which several or, especially, individual protein tyrosine kinases and/or (furthermore) protein serine/threonine kinases are involved; these compounds of the formula I can also be used in the treatment of those disorders of the central or peripheral nervous system in which signal transmission by several or, especially, a single protein tyrosine kinase and/or (furthermore) protein serine/threonine kinases is involved.

In general, the present invention relates also to the use of the compounds of the formula I for the inhibition of the protein kinases mentioned.

The compounds according to the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic agents.

In the preferred subjects of the invention mentioned hereinafter, general definitions can be replaced by the more specific definitions given at the beginning, where appropriate and expedient.

Preferred compounds of the formula I are those according to claim 1, in which R$_1$ is hydrogen, R$_2$ is pyrrolyl, thienyl, furyl, tetrazol-5-yl which is unsubstituted or substituted by lower alkyl, or thiazol-2-yl which is unsubstituted or substituted by lower alkoxyphenyl, or methyl which is substituted by pyrrolyl, thienyl, furyl, morpholino, 4-lower alkylpiperazin-1-yl, tetrazol-5-yl which is unsubstituted or substituted by lower alkyl, or thiazol-2-yl which is unsubstituted or substituted by lower alkoxyphenyl, and the other radicals and symbols are as defined above, and their salts.

Very preferred compounds of the formula I are those in which n is 0 or 1, q is 0 or 1, R is chlorine, R$_1$ is hydrogen, R$_2$ is a) a radical of the formula II

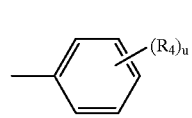

(II)

in which u is 1 and

R$_4$ is N$^3$-lower alkylureido, N$^3$-phenylureido, N$^3$-lower alkylthioureido, lower alkoxycarbonylamino, benzyloxycarbonylamino, morpholine-4-carbonyl, piperazine-1-carbonyl, 4-lower alkylpiperazine-1-carbonyl, lower alkylsulfonylamino, benzenesulfonylamino, toluenesulfonylamino, furan-2-carbonylamino, thiophene-2-carbonylamino, benzylamino, hydroxymethyl or a radical of the formula —N═C(R$_5$)—R$_6$ in which R$_5$ is hydrogen or lower alkyl and R$_6$ is di-lower alkylamino, piperidino, 4-lower alkylpiperazino or morpholino, or is b) a radical of the formula III

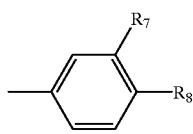

(III)

in which $R_7$ is lower alkoxy and $R_8$ is hydroxyl or benzyloxy, or is c) aminomethyl in which the amino group is substituted by one or two hydroxy-lower alkyl or benzyl radicals which in the phenyl moiety are unsubstituted or substituted by hydroxyl or lower alkoxy, or is d) piperazine-1-carbonyl, 4-lower alkylpiperazine-1-carbonyl, morpholine-4-carbonyl, thiocarbamoyl, thiazol-2-yl, 4-(4-methoxyphenyl)thiazol-2-yl, 4-ethylthiazol-2-yl, 4,5-dimethylthiazol-2-yl, tetrazol-5-yl, 2-methyltetrazol-5-yl or 1-methyltetrazol-5-yl, or is e) 4-lower alkylpiperazinomethyl or morpholinomethyl, or is f) a radical of the formula —CH=N—OR$_9$, in which $R_9$ is hydrogen or lower alkyl, or g) if q is 1, additionally to the definitions given above in sections a) to f) can also be phenyl which is substituted by lower alkoxy, and $R_3$ is hydrogen or lower alkyl,
and their salts.

The most preferred compounds of the formula I are those described in the Examples and their pharmaceutically acceptable salts.

The compounds of the formula I and their salts are prepared by processes known per se. The process according to the invention comprises a) reacting a pyrrolo[2,3-d]pyrimidine derivative of the formula IV

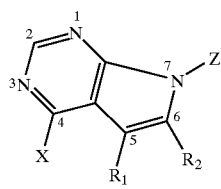

(IV)

in which X is a suitable leaving group, Z is hydrogen or 1-aryl-lower alkyl and the other substituents are as defined above for compounds of the formula I, free functional groups present in the radicals $R_1$ and $R_2$ if necessary being protected by easily removable protective groups, with an aniline derivative of the formula V

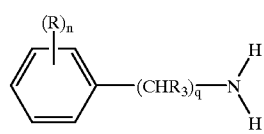

(V)

in which R, $R_3$, n and q are as defined above for compounds of the formula I, free functional groups present in the radical R if necessary being protected by easily removable protective groups, and removing protective groups present and, if present, the 1-aryl-lower alkyl radical Z, or b) reacting a pyrrolo[2,3-d]pyrimidin-4-one derivative of the formula VI

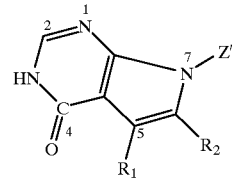

(VI)

in which Z' is 1-aryl-lower alkyl and $R_1$ and $R_2$ are as defined above for compounds of the formula I, free functional groups present in the radicals $R_1$ and $R_2$ if necessary being protected by easily removable protective groups, in the presence of a dehydrating agent and a tertiary amine, with a phenylamine of the formula V above and removing protective groups present, or c) for the preparation of a compound of the formula I in which the radical R is hydroxyl or in which one of the radicals $R_1$ or $R_2$ is amino-lower alkyl in which the amino group is substituted by one or two benzyloxycarbonyl-lower alkyl or benzyl radicals which are substituted by hydroxyl in the phenyl moiety and the other substituents are as defined above for compounds of the formula I, reacting a compound of the formula I in which the radical R is methoxy or in which one of the radicals $R_1$ or $R_2$ is amino-lower alkyl whose amino group is substituted by one or two benzyloxycarbonyl-lower alkyl or benzyl radicals which are substituted by methoxy in the phenyl moiety, and the other substituents are as defined above for compounds of the formula I, free functional groups present in the radicals R, $R_1$ and $R_2$ if necessary being protected by easily removable protective groups, with boron tribromide, and removing protective groups present, or d) for the preparation of a compound of the formula I in which one of the radicals $R_1$ and $R_2$ is aminomethyl in which the amino group is substituted by one or two hydroxy-lower alkyl, amino-lower alkyl, carboxy-lower alkyl, lower alkoxycarbonyl-lower alkyl, benzyloxycarbonyl-lower alkyl or benzyl radicals which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or in which one of the radicals $R_1$ and $R_2$ is 4-lower alkylpiperazinomethyl, morpholinomethyl or piperidinomethyl and the other substituents are as defined above for compounds of the formula I, reacting a compound of the formula I in which one of the radicals $R_1$ and $R_2$ is formyl and the other substituents are as defined above for compounds of the formula I, free functional groups present in the radical R if necessary being protected by easily removable protective groups, with an amine of the formula VII $HN(R_{10})R_{11}$ (VII)

in which
α) $R_{10}$ is hydrogen, hydroxy-lower alkyl, amino-lower alkyl, carboxy-lower alkyl, lower alkoxycarbonyl-lower alkyl, benzyloxycarbonyl-lower alkyl or benzyl, the benzyloxycarbonyl-lower alkyl or benzyl radicals in the phenyl moiety being unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, and $R_{11}$ is hydroxy-lower alkyl, amino-lower alkyl, carboxy-lower alkyl, lower alkoxycarbonyl-lower alkyl, benzyloxycarbonyl-lower alkyl or benzyl, the benzyl oxycarbonyl-lower alkyl or benzyl radicals in the phenyl moiety being unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or β) in which the radicals $R_{10}$ and $R_{11}$ together are pentane-1,5-diyl, 3-N-lower alkyl-3-azapentane-1,5-diyl or 3-oxapentane-1,5-diyl, catalytically hydrogenating the product and then removing protective groups present, or e) for the preparation of a compound of the formula I in which one of the radicals $R_1$ and $R_2$ is a radical of the formula —CH=N—$OR_9$ in which $R_9$ is hydrogen or lower alkyl, and the other substituents are as defined above for compounds of the formula I, reacting a compound of the formula I, in which one of the radicals $R_1$ and $R_2$ is formyl and the other substituents are as defined above for compounds of the formula I, free functional groups present in the radical R if necessary being protected by easily removable protective groups, with a hydroxylamine derivative of the formula VIII

in which $R_{12}$ is hydrogen or lower alkyl, and removing protective groups present, or f) for the preparation of a compound of the formula I in which one of the radicals $R_1$ and $R_2$ is piperidine-1-carbonyl, piperazine-1-carbonyl, 4-lower alkylpiperazine-1-carbonyl or morpholine-4-carbonyl, and the other substituents are as defined above for compounds of the formula I, reacting a compound of the formula I in which one of the radicals $R_1$ and $R_2$ is carboxyl and the other substituents are as defined above for compounds of the formula I, free functional groups present in the radical R if necessary being protected by easily removable protective groups, or a reactive carboxylic acid derivative of such a compound, with an amine of the formula VII

in which the radicals $R_{10}$ and $R_{11}$ together are pentane-1,5-diyl, 3-azapentane-1,3-diyl, 3-N-lower alkyl-3-azapentane-1,3-diyl or 3-oxapentane-1,3-diyl, and then removing protective groups present, or g) for the preparation of a compound of the formula I in which one of the radicals $R_1$ and $R_2$ is thiocarbamoyl and the other substituents are as defined above for compounds of the formula I, reacting a compound of the formula I in which one of the radicals $R_1$ and $R_2$ is aminocarbonyl and the other substituents are as defined above for compounds of the formula I, free functional groups present in the radical R if necessary being protected by easily removable protective groups, with Lawesson's reagent, and then removing protective groups present, or h) for the preparation of a compound of the formula I in which one of the radicals $R_1$ and $R_2$ is $R_{13}$-thiazol-2-yl in which $R_{13}$ in each case is unsubstituted or substituted lower alkyl or phenyl and the other substituents are as defined above for compounds of the formula I, reacting a compound of the formula I in which one of the radicals $R_1$ and $R_2$ is thiocarbamoyl and the other substituents are as defined above for compounds of the formula I, free functional groups present in the radical R if necessary being protected by easily removable protective groups, with a compound of the formula IX

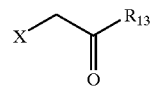

in which X is a leaving group and $R_{13}$ in each case is unsubstituted or substituted lower alkyl or phenyl, free functional groups present in the radical $R_{13}$ if necessary being protected by easily removable protective groups, and then removing protective groups present, or i) for the preparation of a compound of the formula I in which one of the radicals $R_1$ and $R_2$ is tetrazol-5-yl and the other substituents are as defined above for compounds of the formula I, reacting a compound of the formula I in which one of the radicals $R_1$ and $R_2$ is cyano and the other substituents are as defined above for compounds of the formula I, free functional groups present in the radical R if necessary being protected by easily removable protective groups, with a suitable alkali metal azide, and then removing protective groups present, or j) for the preparation of a compound of the formula I in which one of the radicals $R_1$ and $R_2$ is 2-lower alkyltetrazol-5-yl and the other substituents are as defined above for compounds of the formula I, reacting a compound of the formula I in which one of the radicals $R_1$ and $R_2$ is tetrazol-5-yl and the other substituents are as defined above for compounds of the formula I, free functional groups present in the radical R if necessary being protected by easily removable protective groups, with the appropriate lower alkyl iodide, and then removing protective groups present, or k) for the preparation of a compound of the formula I in which one of the radicals $R_1$ and $R_2$ is a radical of the formula II

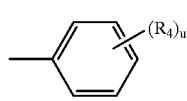 (II)

in which at least one radical $R_4$ is lower alkylsulfonylamino, benzenesulfonylamino or toluenesulfonylamino and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with a compound of the formula X $$R_{14}\text{—}SO_2\text{—}X \qquad (X)$$

in which X is chlorine or bromine and $R_{14}$ is lower alkyl, phenyl or 4-methylphenyl, and then removing protective groups present, or l) for the preparation of a compound of the formula I in which one of the radicals $R_1$ and $R_2$ is a radical of the formula II

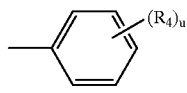 (II)

in which at least one radical $R_4$ is a radical of the formula —N=C($R_5$)—$R_6$ in which $R_5$ is hydrogen and $R_6$ is as defined above for compounds of the formula I and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with an acetal of the formula XI

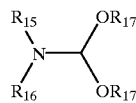 (XI)

in which $R_{15}$ and $R_{16}$ are each individually lower alkyl or together pentane-1,5-diyl, 3-N-lower alkyl-3-azapentane-1,5-diyl or 3-oxapentane-1,5-diyl, and each $R_{17}$ is lower alkyl, and then removing protective groups present, or m) for the preparation of a compound of the formula I in which one of the radicals $R_1$ and $R_2$ is a radical of the formula II

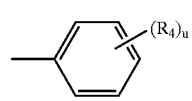 (II)

in which at least one radical $R_4$ is $N^3$-lower alkylureido or $N^3$-phenylureido and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with an isocyanate of the formula XII $$R_{18}\text{—}N\text{=}C\text{=}O \qquad (XII)$$

in which $R_{18}$ is lower alkyl or phenyl, and then removing protective groups present, or n) for the preparation of a compound of the formula I in which one of the radicals $R_1$ and $R_2$ is a radical of the formula II

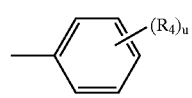 (II)

in which at least one radical $R_4$ is $N^3$-lower alkylthioureido or $N^3$-phenylthioureido and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with an isothiocyanate of the formula XIII $$R_{18}\text{—}N\text{=}C\text{=}S \qquad (XIII)$$

in which $R_{18}$ is lower alkyl or phenyl, and then removing protective groups present, or o) for the preparation of a compound of the formula I in which one of the radicals $R_1$ and $R_2$ is a radical of the formula II

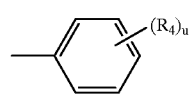 (II)

in which at least one radical $R_4$ is lower alkoxycarbonylamino or benzyloxycarbonyl-amino and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with a chloroformic acid ester of the formula XIV

Cl—C(=O)—OR$_{20}$ (XIV)

in which $R_{20}$ is lower alkyl or benzyl, and then removing protective groups present,
and after carrying out one of the process variants a) to o), if necessary for the preparation of a salt, converting a free compound of the formula I obtained into a salt or, if necessary for the preparation of a free compound, converting a salt of a compound of the formula I obtained into the free compound.

Detailed Description of the Process Steps

The above processes are described in detail below (see also German Offenlegungs-schrift No. 30 36 390, published on May 13, 1982, and A. Jorgensen et al., J. Heterocycl. Chem. 22, 859 [1985]). In the more precise description that follows, unless otherwise indicated the radicals R, $R_1$ and $R_2$ and n are as defined for compounds of the formula I.

General Points:

The end products of the formula I may contain substituents that can also be used as protective groups in starting materials for the preparation of other end products of the formula I. Unless the context indicates otherwise, the term "protective group" is used in this text to denote only an easily removable group that is not a constituent of the particular desired end product of the formula I.

Process a)

In the compound of the formula IV a suitable leaving group X is preferably halogen, such as bromine, iodine or especially chlorine. 1-Aryl-lower alkyl Z is preferably 1-phenyl-lower alkyl, such as especially 1-phenylethyl or, in particular, benzyl.

Free functional groups present in the radicals $R_1$ and $R_2$, which if necessary are protected by easily removable protective groups, are especially amino or lower alkylamino.

Protective groups and their introduction and removal are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. It is a characteristic of protective groups that they can be removed easily, i.e. without undesired secondary reactions taking place, for example by solvolysis, reduction, photolysis or alternatively under physiological conditions.

A protected amino group may be present, for example, in the form of an easily cleavable acylamino, arylmethylamino, etherified mercaptoamino or 2-acyl-lower alk-1-enylamino group.

In a corresponding acylamino group, acyl is, for example, the acyl radical of an organic carboxylic acid having, for example, up to 18 carbon atoms, especially an unsubstituted or substituted, for example halo- or aryl-substituted, alkanecarboxylic acid or an unsubstituted or substituted, for example halo-, lower alkoxy- or nitro-substituted, benzoic acid, or of a carbonic acid hemiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxy-carbonyl, arylmethoxycarbonyl having one or two aryl radicals which are preferably phenyl that is unsubstituted or mono- or poly-substituted, for example, by lower alkyl, especially tert-lower alkyl, such as tert-butyl, lower alkoxy, such as methoxy, hydroxyl, halogen, for example chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di(4-methoxyphenyl)methoxycarbonyl, aroylmethoxycarbonyl in which the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)ethoxycarbonyl in which the substituents are each independently of the others an unsubstituted or substituted, for example lower alkyl-, lower alkoxy-, aryl-, halo- or nitro-substituted, aliphatic, araliphatic, cycloaliphatic or aromatic hydrocarbon radical having up to 15 carbon atoms, such as corresponding, unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)ethoxycarbonyl, or 2-triarylsilylethoxycarbonyl, such as 2-triphenylsilylethoxycarbonyl.

In an arylmethylamino group, which is a mono-, di- or especially tri-arylmethyl-amino group, the aryl radicals are especially unsubstituted or substituted phenyl radicals. Such groups are, for example, benzyl-, diphenylmethyl- and especially trityl-amino.

An etherified mercapto group in an amino group protected by such a radical is especially arylthio or aryl-lower alkylthio, in which aryl is, especially, phenyl that is unsubstituted or substituted, for example, by lower alkyl, such as methyl or tert-butyl, lower alkoxy, such as methoxy, halogen, such as chlorine, and/or by nitro. A corresponding amino protective group is, for example, 4-nitrophenylthio.

In a 2-acyl-lower alk-1-en-1-yl radical that can be used as an amino protective group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid hemiester, such as a carbonic acid lower alkyl hemiester. Corresponding protective groups are especially 1-lower alkanoylprop-1-en-2-yl, such as 1-acetylprop-1-en-2-yl, or 1-lower alkoxycarbonylprop-1-en-2-yl, for example 1-ethoxycarbonylprop-1-en-2-yl.

Preferred amino protective groups are acyl radicals of carbonic acid hemiesters, especially tert-butyloxycarbonyl, benzyloxycarbonyl that is unsubstituted or substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl, also trityl or formyl.

The reaction between the derivative of the formula IV and the aniline derivative of the formula V takes place in suitable inert polar solvents, especially alcohols, for example lower alkanols, such as methanol, propanol, isopropanol or especially ethanol or n-butanol. In some cases the addition of a solubilizer, such as 1,3-dimethyl-3,4,5,6-tetrahydro-2(1H)-pyrimidinone (DMPU), is advantageous. The reaction takes place at elevated temperatures, for example in a temperature range from 70 to 150° C, preferably under reflux conditions.

If Z in the compound of the formula IV is 1-aryl-lower alkyl, this radical is removed from the resulting precursor of the compound of the formula I (with Z instead of the hydrogen atom on the nitrogen). This is effected, for example, by treatment with protonic acids, such as hydrochloric acid, phosphoric acids or polyphosphoric acid, at preferred temperatures from 20° C. to 150° C. and where appropriate in the presence of water (this is especially the preferred method for Z=1-phenylethyl); or preferably by treatment with Lewis acids, especially AlCl$_3$, in an aromatic solvent, especially in benzene and/or toluene, at elevated temperature, especially under reflux [this is especially the preferred variant for Z=benzyl; see also the analogous process in Chem. Pharm. Bull. 39(5), 1152 (1991)].

The removal of the protective groups that are not constituents of the desired end product of the formula I is effected in a manner known per se, for example by means of solvolysis, especially hydrolysis, alcoholysis or acidolysis, or by means of reduction, especially hydrogenolysis or chemical reduction, where appropriate stepwise or simultaneously.

A protected amino group is liberated in a manner known per se and, according to the nature of the protective groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-trisubstituted silylethoxycarbonylamino can be cleaved by treatment with a suitable acid, for example formic acid or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or with an organic acid, for example formic, acetic or trifluoroacetic acid, where appropriate in the presence of water; and an amino group protected by an organic silyl group can be liberated, for example, by means of hydrolysis or alcoholysis. An amino group protected by 2-haloacetyl, for example 2-chloroacetyl, can be liberated by treatment with thiourea in the presence of a base, or with a thiolate salt, such as an alkali metal thiolate, of thiourea, and subsequent solvolysis, such as alcoholysis or hydrolysis, of the resulting condensation product. An amino group protected by 2-substituted silylethoxycarbonyl can be converted into the free amino group also by treatment with a salt of hydrofluoric acid that yields fluoride anions.

Process b)

1-Aryl-lower alkyl Z' in a compound of the formula VI is especially 1-phenylethyl and also benzyl.

The compound of the formula VI is in tautomeric equilibrium (lactam/lactim form), the lactam form (formula VI) presumably predominating. Formula VI is used to represent the two possible equilibrium forms.

The lactim form has the formula VIa

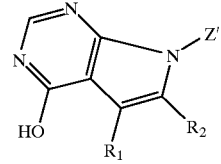

(VIa)

in which the radicals are as defined for compounds of the formula VI.

The present invention also relates to the novel compounds of the formulae VI and VIa.

The dehydrating agent employed especially a strong chemical dehydrating agent, in particular phosphorus pentoxide ($P_4O_{10}$).

A suitable tertiary amine is primarily ammonia substituted by three radicals selected independently of one another from alkyl, especially lower alkyl, such as methyl or ethyl, and cycloalkyl having 3 to 7 carbon atoms, especially cyclohexyl, for example N,N-dimethyl-N-cyclohexylamine, N-ethyl-N,N-diisopropylamine or triethylamine, or, furthermore, also pyridine, N-methylmorpholine or 4-dimethylaminopyridine.

The reaction between the pyrrolopyrimidinone of the formula VI and the aniline derivative of the formula V takes place at elevated temperature, for example at 200 to 250° C.

Process c)

The reaction is carried out with the exclusion of moisture.

Process d)

The reaction is preferably carried out in a suitable inert solvent, for example a suitable alcohol, such as especially methanol, in the presence of 1,3-dimethyl-3,4,5,6-tetrahydro-2(1H)-pyrimidinone (DMPU) and acetic acid at temperatures from approximately +10° C. to +70° C., preferably at room temperature.

The hydrogenation is carried out at elevated pressure or preferably normal pressure in the presence of a suitable hydrogenation catalyst, such as especially Raney nickel, in the above reaction solution at temperatures from approximately 10° C. to +70° C., preferably at 50° C.

Process e)

The reaction is preferably carried out in a suitable inert solvent, for example a suitable alcohol, such as especially methanol, at temperatures from approximately +10° C. to +100° C., preferably at the boiling temperature of the reaction mixture. In this case the hydroxylamine derivative of the formula VII is preferably employed as a salt and converted into the free base by addition of an aqueous solution of sodium acetate to the reaction mixture.

Process f)

A reactive carboxylic acid derivative of a compound of the formula I in which one of the radicals $R_1$ and $R_2$ is carboxyl and the other substituents are as defined above for compounds of the formula I is, for example, a suitable ester, such as especially an ethyl ester.

Where possible, for example if morpholine is the amine of the formula VII, the amine of the formula VII can be used itself as a solvent. In other cases a suitable inert solvent, e.g. dimethylformamide, together with TPTU (O-(1,2-dihydro-2-oxo-1-pyridyl)N,N,N',N'-tetramethyluronium tetrafluoroborate is used. The reaction is preferably carried out at temperatures from approximately +10° C. to +150° C., preferably from room temperature to 100° C.

Process g)

Lawesson's reagent is 2,4-di[4-methoxyphenyl]-1,3-dithia-2,4-diphosphetane-2,4-disulfide and is commercially available, inter alia from SIGMA, FLUKA etc. The reaction is preferably carried out in a suitable inert solvent, e.g. a suitable ether, such as especially a cyclic ether, e.g. tetrahydrofuran, at temperatures from approximately 50° C. to 150° C., preferably at the boiling temperature of the reaction mixture.

Process h)

$R_{13}$ is preferably lower alkyl, such as especially ethyl, or unsubstituted or halo-, lower alkyl-, hydroxymethyl-, aminomethyl-, hydroxyl-, lower alkanoyloxy-, lower alkoxy-, carboxyl-, lower alkanoyl-, benzoyl-, lower alkoxycarbonyl-, carbamoyl-, N-lower alkylcarbamoyl-, N,N-di-lower alkylcarbamoyl-, cyano-, amino-, lower alkanoylamino-, lower alkylamino-, N,N-di-lower alkylamino- or trifluoromethyl-substituted phenyl, in particular 4-methoxyphenyl.

The reaction is preferably carried out in a suitable inert solvent, e.g. a suitable alcohol, such as especially methanol, or a suitable ether, e.g. dioxane, at temperatures from approximately +20° C. to +180° C., preferably at the boiling temperature of the reaction mixture.

Process i)

The reaction is preferably carried out in a suitable inert solvent, e.g. a suitable alcohol, such as especially 1-methoxyethanol, in the presence of lithium chloride, e.g. one and a half times the molar amount of lithium chloride, at temperatures from approximately +20° C. to +180° C., preferably at the boiling temperature of the reaction mixture.

Process j)

The reaction is preferably carried out in a suitable inert solvent, e.g. dimethylformamide, in the presence of sodium hydrogen carbonate, at temperatures from approximately 0° C. to +180° C., preferably at room temperature. In this case the lower alkyl iodide, such as especially methyl iodide, is preferably added as a solution, e.g. 1 M solution, in a suitable ether, such as dioxane.

Process k)

X is preferably chlorine. The reaction is preferably carried out in a suitable inert and anhydrous solvent, e.g. dimethylacetamide, at temperatures from approximately −30° C. to +70° C., preferably at 0° C.

Process l)

$R_{17}$ is preferably methyl. The reaction is preferably carried out in a suitable inert and anhydrous solvent, e.g. an ether, such as tetrahydrofuran, in the presence of triethylamine at temperatures from approximately −10° C. to +70° C., preferably at room temperature.

Process m)

The reaction is preferably carried out in a suitable inert and anhydrous solvent, e.g. an ether, such as tetrahydrofuran, advantageously in the presence of dimethylacetamide at temperatures from approximately 0° C. to +150° C., preferably at the boiling temperature of the reaction mixture.

Process n)

The reaction is preferably carried out in a suitable inert and anhydrous solvent, e.g. an ether, such as tetrahydrofuran, advantageously in the presence of dimethylacetamide at temperatures from approximately 0° C. to +150° C., preferably at the boiling temperature of the reaction mixture.

Process o)

The reaction is preferably carried out in a suitable inert and anhydrous solvent, e.g. an ether, such as dioxane, advantageously in the presence of 2,6-lutidine, at temperatures from approximately −30° C. to +150° C., preferably at room temperature.

Starting Materials:

The starting materials of the formula IV are novel and the present invention also relates thereto. They can be prepared by processes analogous to those described in German Offenlegungsschrift No. 28 18 676 (published on Nov. 8, 1979) and German Offenlegungsschrift No. 30 36 390 (published on May 13, 1982).

The starting material of the formula IV in which X is chlorine is obtained, for example, from a compound analogous to formula IV in which X is hydroxyl (see the compounds of the formula VIa) by reaction with phosphorus oxychloride (phosphoryl chloride, $P(=O)Cl_3$) with the exclusion of moisture at reflux temperature. If desired, the further reaction of the starting material of the formula IV thus obtained in which X is chlorine can be carried out with an aniline derivative of the formula V in the same vessel, i.e. as a one-pot reaction. For this purpose, after the reaction with phosphorus oxychloride is complete, the reaction mixture is evaporated to dryness, suspended using a suitable solvent, such as n-butanol, and reacted further with the aniline derivative of the formula V.

A compound analogous to formula IV in which X is hydroxyl is obtained, for example, from a compound of the formula XV

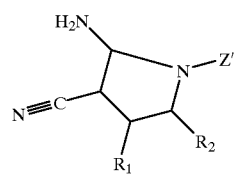

(XV)

in which the symbols are as defined above, by reaction with formic acid which is preferably employed in excess relative to the compound of the formula XV, for example in a 10 to 30 molar excess, where appropriate in the presence of inert solvents, such as dimethylformamide, at elevated temperature, for example at temperatures from 80° C. to the boiling temperature.

Alternatively, a compound analogous to formula IV in which X is hydroxyl and the other symbols are as defined above is obtained, for example, from a compound of the formula XVI

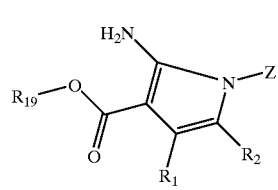

(XVI)

in which $R_{19}$ is lower alkyl, such as especially ethyl, and the other symbols are as defined above, by reaction with a large excess of formamide in a mixture of anhydrous dimethylformamide and formic acid. The reaction is carried out at elevated temperature, for example at from 100° C. to 150° C., and preferably under protective gas.

The present invention also relates to the novel starting materials of the formulae XV and XVI.

The 1-(Z')-2-amino-3-cyanopyrroles of the formula XV used as intermediates can be prepared in good yields by methods that are known per se and have been published [see, for example, Roth, H. J., and Eger, K., Arch. Pharmaz. 308, 179 (1975)]. For this purpose, for example, a compound of the formula XVII

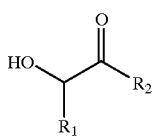

(XVII)

is reacted first with an amine of the formula Z'-NH$_2$ to give a compound of the formula XVIII

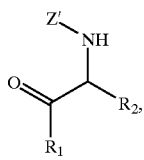

(XVIII)

which is then converted with malononitrile of the formula CH$_2$(CN)$_2$ into the desired intermediate of the formula XV. In detail, the reaction with the amine Z'-NH$_2$ is carried out under customary condensation conditions, for example in the presence of catalytic amounts of a strong acid, for example hydrochloric acid or p-toluenesulfonic acid, at elevated temperature (preferably at boiling heat) in a suitable solvent, for example benzene or toluene, with separation of water, to give the respective α-amino ketone of the formula XVIII. The latter is not isolated but is immediately condensed with malononitrile with heating and with further separation of water, if necessary with the addition of a small amount of a base, such as piperidine, a compound of the formula XV being obtained.

The compounds of the formula XVI used as intermediates are obtained, for example, by reacting a 2-amidinoacetic acid lower alkyl ester of the formula XIX

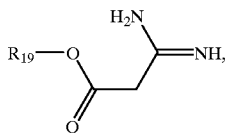

(XIX)

wherein R$_{19}$ is as defined above, with a 2-X-1-R$_2$-ethan-1-one derivative of the formula XX

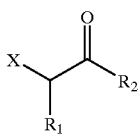

(XX)

in which the symbols are as defined above. The leaving group X is preferably bromine. The 2-amidinoacetic acid lower alkyl ester of the formula XIX is liberated from its acid addition salt, such as especially its hydrochloride, before the start of the reaction with the aid of equinormal amounts of a base, such as especially sodium ethoxide, with ice-cooling. The reaction is carried out in a suitable solvent, such as especially a lower alkanol, such as preferably ethanol, at preferred temperatures of from 0° C. to 50° C., especially at room temperature.

A starting compound of the formula I in which one of the radicals R$_1$ and R$_2$ is formyl, carboxyl, lower alkoxycarbonyl, cyano, carbamoyl, thiocarbamoyl, aminophenyl or tetrazol-5-yl and the other substituents are as defined above for compounds of the formula I, free functional groups present in the radical R if necessary being protected by easily removable protective groups, are obtained as explained in an exemplary manner in the examples section. A person skilled in the art can transfer the specific exemplified reactions without major effort to compounds having other radicals R and R$_1$ or R$_2$ than those which are specifically exemplified, provided that free functional groups present in the radical R are protected by easily removable protective groups, if necessary, that is if these interfere with the desired reaction. In many cases, especially if, for example, R is halogen, no protection is necessary.

General Process Conditions:

Free compounds of the formula I having salt-forming properties that are obtainable according to the process can be converted into their salts in a manner known per se, for example by treating with acids or suitable derivatives thereof, for example by addition of the appropriate acid to the compound of the formula I dissolved in a suitable solvent, for example an ether, such as a cyclic ether, especially dioxane or in particular tetrahydrofuran.

Mixtures of isomers obtainable according to the invention can be separated into the individual isomers in a manner known per se; racemates can be separated, for example, by forming salts with optically pure salt-forming reagents and separating the mixture of diastereomers thus obtainable, for example by means of fractional crystallization.

The reactions described above can be carried out under reaction conditions known per se, in the absence or, customarily, the presence of solvents or diluents, preferably those that are inert towards the reagents used and are solvents therefor, in the absence or presence of catalysts, condensing agents (for example phosphorus pentoxide) or neutralizing agents, for example bases, especially nitrogen bases, such as triethylamine hydrochloride, depending on the nature of the reaction and/or of the reactants at reduced, normal or elevated temperature, for example in a temperature range from approximately −80° C. to approximately 200° C., preferably from approximately −20° C. to approximately 150° C., for example at the boiling point of the solvent used, under atmospheric pressure or in a closed vessel, where appropriate under pressure, and/or in an inert atmosphere, for example under a nitrogen atmosphere.

The specific reaction conditions given in each case are preferred.

Solvents and diluents are, for example, water, alcohols, for example lower alkyl hydroxides, such as methanol, ethanol, propanol or especially butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, especially formic acid or acetic acid, amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitrites, such as acetonitrile, acid anhydrides, such as acetic anhydride, esters, such as ethyl acetate, bis-alkanesulfines, such as dimethyl sulfoxide, nitrogen-containing heterocyclic compounds, such as pyridine, hydrocarbons, for example lower alkanes, such as heptane, or aromatic compounds, such as benzene, toluene or xylene(s), or mixtures of these solvents, it being possible for the solvents suitable in each case for the abovementioned reactions to be selected.

Customary processes are used for working up the obtainable compounds of the formula I or their salts, for example solvolysis of excess reagents; recrystallizing; chromatographing, for example partition, ion or gel chromatography; partitioning between inorganic and organic solvent phases; single or multiple extraction, especially after acidifying or increasing the basicity or the salt content; drying over hygroscopic salts; digesting; filtering; washing; dissolving; evaporating (if necessary in vacuo or under a high vacuum); distillation; crystallization, for example of compounds obtained in oil form or from the mother liquor, seeding with a crystal of the end product also being possible; or a combination of two or more of the working-up steps mentioned, which can also be employed repeatedly, etc.

Starting materials and intermediates can be used in pure form, for example after working-up, as just mentioned, in partly purified form or alternatively, for example, directly as a crude product.

The compounds, including their salts, may also be obtained in the form of hydrates, or their crystals may include, for example, the solvent used for crystallization. The present invention also relates to these hydrates or solvates of the compounds of the formula I, and to the starting materials described as belonging to the subject matter of the invention.

In view of th e close relationship between the compounds of the formula I in free form and in the form of their salts, hereinabove and hereinbelow the free compounds and their salts are to be understood as meaning also the corresponding salts and free compounds, respectively, as appropriate and expedient, provided that the compounds contain salt-forming groups. The same applies to the hydrates and solvates.

In the process of the present invention, the starting materials employed are preferably those that lead to the novel compounds of the formula I described at the beginning as being especially valuable.

The invention also relates to those forms of the process in which a compound obtainable as an intermediate at any stage of the process is used as a starting material and the remaining process steps are carried out or in which a starting material is formed under the reaction conditions or is used in the form of a derivative, for example a salt thereof.

Pharmaceutical Compositions, their Preparation and
the Use According to the Invention of the
Compounds of the Formula I and of Compositions
Comprising these Compounds as Active Ingredient The present invention also relates to pharmaceutical compositions that comprise one of the compounds of the formula I as active ingredient and that can be used especially for the treatment of the diseases mentioned earlier. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient on its own or, preferably, together with a pharmaceutically acceptable carrier. The dosage of the active ingredient depends upon the disease to be treated and upon the species, its age, weight and individual condition, the individual pharmacokinetic data, the disease to be treated and also upon the mode of administration.

The invention also relates to pharmaceutical compositions for use in a method for the therapeutic treatment of the human or animal body, to a process for the preparation thereof (especially as compositions for the treatment of tumors) and to a method of treating neoplastic diseases, especially those mentioned above.

A pharmaceutical composition is preferred which is suitable for administration to a warm-blooded animal, especially a human, suffering from a disease that is responsive to inhibition of a protein kinase, for example psoriasis or a tumor, comprising a compound of the formula I, or a salt thereof if salt-forming groups are present, in an amount effective for the inhibition of the protein kinase, together with at least one pharmaceutically acceptable carrier.

The pharmaceutical compositions comprise from approximately 1% to approximately 95% of the active ingredient, administration forms in single dose form preferably comprising from approximately 20% to approximately 90% of active ingredient and administration forms that are not in single dose form preferably comprising from approximately 5% to approximately 20% of active ingredient. Unit dose forms are, for example, sugar-coated tablets, tablets, ampoules, vials, suppositories or capsules. Other administration forms are, for example, ointments, creams, pastes, foams, tinctures, lipsticks, drops, sprays, dispersions, etc. Examples are capsules, comprising from approximately 0.05 g to approximately 1.0 g of the active ingredient.

The pharmaceutical compositions of the present invention are prepared in a manner known per se, for example by means of conventional mixing, granulating, sugar-coating, dissolving or lyophilizing processes.

Solutions of the active ingredient are preferably used, and also suspensions or dispersions, to be precise especially isotonic aqueous solutions, dispersions or suspensions which, for example in the case of lyophilized compositions which comprise the active ingredient on its own or together with a carrier, for example mannitol, can be prepared before use. The pharmaceutical compositions may be sterilized and/or may comprise excipients, for example preservatives, stabilizers, wetting agents and/or emulsifiers, solubilizers, salts for regulating the osmotic pressure and/or buffers, and are prepared in a manner known per se, for example by means of conventional dissolving and lyophilizing processes. The solutions or suspensions mentioned may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chain fatty acid having 8–22, especially 12–22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a mono- or polyhydric, for example a mono-, di- or trihydric alcohol, for example methanol, ethanol, propanol, butanol or pentanol or their isomers, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Labrafil M 1944 CS" (unsaturated polyglycolized glycerides prepared by alcoholysis of apricot kernel oil and consisting of glycerides and polyethylene glycol ester, Gattefossé, France), "Labrasol" (saturated polyglycolized glycerides prepared by alcoholysis of TCM and consisting of glycerides and polyethylene glycol ester, Gattefossé, France) and/or "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soya bean oil and in particular groundnut oil.

The injection compositions are prepared in a customary manner under sterile conditions; the same applies also to dispensing the compositions into ampoules or vials, for example, and sealing the containers.

Pharmaceutical compositions for oral administration can be obtained, for example, by combining the active ingredient with one or more solid carriers, where appropriate granulating a mixture obtained, and, if desired, processing the mixture or granules, where appropriate by addition of additional excipients, to give tablets or sugar-coated tablet cores.

Suitable carriers are especially fillers, such as sugars, for example lactose, sucrose, mannitol or sorbitol, cellulose preparations and/or calcium phosphates, for example tricalcium phosphate or calcium hydrogenphosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the abovementioned starches, also carboxymethyl starch, crosslinked polyvinylpyrrolidone, alginic acid or a salt thereof, such as sodium alginate. Additional adjuncts are primarily flow conditioners and lubricants, for example silicic acid, talc, stearic acid or salts thereof, such as magnesium or calcium stearate, and/or polyethylene glycol, or derivatives thereof.

Sugar-coated tablet cores can be provided with suitable, optionally enteric, coatings, using, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or sugar-coated tablet coatings, for example for identification purposes or to indicate different doses of active ingredient.

Orally administrable pharmaceutical compositions also include dry-filled capsules consisting of gelatin, and also soft, sealed capsules consisting of gelatin and a plasticizer, such as glycerol or sorbitol. The dry-filled capsules may contain the active ingredient in the form of granules, for example as a mixture with fillers, such as corn starch, binders and/or glidants, such as talc or magnesium stearate, and, where appropriate, stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Other oral administration forms are, for example, syrups prepared in customary manner which comprise the active ingredient, for example in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are primarily suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, where appropriate together with adjuncts, can also be in the form of a lyophilizate and can be made into a solution prior to parenteral administration by addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

Ointments are oil-in-water emulsions that contain up to 70%, but preferably 20%–50%, of water or aqueous phase. Suitable as fatty phase are primarily hydrocarbons, for example petroleum jelly, paraffin oil or hard paraffins, which, in order to improve the water-binding capacity, preferably contain suitable hydroxy compounds, such as fatty alcohols or esters thereof, for example cetyl alcohol or wool wax alcohols, such as wool wax. Emulsifiers are appropriate lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, and also preservatives and perfumes.

Fatty ointments are anhydrous and contain as base especially hydrocarbons, for example paraffin, petroleum jelly or paraffin oil, also natural or partially synthetic fats, for example coconut fatty acid triglyceride, or preferably hardened oils, for example hydrogenated groundnut oil or castor oil, also fatty acid partial esters of glycerol, for example glycerol mono- and/or distearate, and also, for example, the fatty alcohols increasing the water-absorption, emulsifiers and/or additives mentioned in connection with the ointments.

Creams are oil-in-water emulsions that contain more than 50% of water. As oily base there are used primarily fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable emulsifiers are surface-active substances having predominantly hydrophilic properties, such as appropriate non-ionic emulsifiers, for example fatty acid esters of polyalcohols or ethylene oxide adducts thereof, such as polyglycerol fatty acid esters or polyoxyethylene sorbitan fatty acid esters (Tweens), and also polyoxyethylene fatty alcohol ethers or fatty acid esters, or appropriate ionic emulsifiers, such as alkali metal salts of fatty alcohol sulfates, for example sodium lauryl sulfate, sodium cetyl sulfate or sodium stearyl sulfate, which are customarily used in the presence of fatty alcohols, for example cetyl alcohol or stearyl alcohol. Additives to the aqueous phase are, inter alia, agents that reduce the drying out of the creams, for example polyalcohols, such as glycerol, sorbitol, propylene glycol and/or polyethylene glycols, and also preservatives and perfumes.

Pastes are creams and ointments having secretion-absorbing powder constituents, such as metal oxides, for example titanium oxide or zinc oxide, also talc and/or aluminum silicates, the object of which is to bind moisture or secretions present.

Foams are administered from pressurized containers and are liquid oil-in-water emulsions in aerosol form; halogenated hydrocarbons, such as chlorofluoro-lower alkanes, for example dichlorodifluoromethane and dichlorotetrafluoroethane, or preferably non-halogenated gaseous hydrocarbons, air, $N_2O$ or carbon dioxide, are used as propellant gases. As oil phase there are used, inter alia, those used above in the case of ointments and creams, and also the additives mentioned in that connection.

Tinctures and solutions usually have an aqueous-ethanolic base to which there are added, inter alia, polyalcohols, for example glycerol, glycols and/or polyethylene glycol, as humectants for reducing evaporation, and fat-restoring substances, such as fatty acid esters with low molecular weight polyethylene glycols, i.e. lipophilic substances that are soluble in the aqueous mixture, as a replacement for the fatty substances extracted from the skin by the ethanol, and, if necessary, other adjuncts and additives.

The invention also relates to a process or a method of treating the abovementioned pathological conditions, especially those conditions responsive to inhibition of protein kinases. The compounds of the formula I can be administered as such or in the form of pharmaceutical compositions, prophylactically or therapeutically, preferably in an amount effective against the diseases mentioned, to a warm-blooded animal, for example a human, requiring such treatment, the compounds especially being used in the form of pharmaceutical compositions. In the case of a body weight of about 70 kg a daily dose of approximately 0.1 g to approximately 5 g, preferably from approximately 0.5 g to approximately 2 g, of a compound of the present invention is administered.

The following Examples serve to illustrate the invention.

If not mentioned otherwise, the ratio of solvents to one another is given in parts by volume (v/v).

The short forms and abbreviations used have the following definitions:
Eluents (gradients):
HPLC gradients:

Grad$_{20}$ 20%→100% a) in b) for 20 min.
Eluent a): acetonitrile+0.05% TFA; eluent b): water+0.05% TFA. Column (250×4.6 mm) packed with reversed-phase material $C_{18}$-Nucleosil® (5 μm average particle size, silica gel covalently derivatized with octadecylsilanes, Macherey & Nagel, Düren, Germany). Detection by UV absorption at 254 nm. The retention times ($t_{Ret}$) are given in minutes.
Flow rate: 1 ml/min.
Abbreviations

| | |
|---|---|
| abs. | absolute (anhydrous) |
| TLC-$R_f$ | $R_f$ according to thin-layer chromatography |
| DEPC | diethyl pyrocarbonate |
| DIPE | diisopropyl ether |
| DMA | dimethylacetamide |
| DMF | dimethylformamide |
| DMPU | 1,3-dimethyl-3,4,5,6-tetrahydro-2(1H)-pyrimidinone |
| DMSO | dimethyl sulfoxide |
| EI-MS | electron impact ionization mass spectroscopy |
| FAB-MS | fast atom bombardment mass spectroscopy |
| satd | saturated |
| h | hour(s) |
| HPLC | high-pressure liquid chromatography |
| HV | high vacuum |
| min | minute(s) |
| MS | mass spectroscopy |
| RT | room temperature |
| RE | rotary evaporator |
| m.p. | melting point |
| brine | saturated sodium chloride solution |
| TFA | trifluoroacetic acid |
| THF | tetrahydrofuran |
| TPTU | O-(1,2-dihydro-2-oxo-1-pyridyl)-N,N,N',N'-tetramethyluronium tetrafluoroborate |

Abbreviations used in NMR Spectra Data

| | |
|---|---|
| b | broad |
| d | doublet |
| J | coupling constant |
| m | multiplet |
| q | quartet |
| s | singlet |
| t | triplet |

EXAMPLE 1

136.4 mg (0.50 mmol) of 4-(3-chloroanilino)-6-formyl-7H-pyrrolo[2,3-d] pyrimidine and 67 μl of N-methylpiperazine in 5 ml of methanol, 15 ml of DMPU and 63 μl of acetic acid are hydrogenated at 50° C. in the presence of 30 mg of Raney nickel. The catalyst is filtered off, the filtrate is evaporated and the residue is dissolved in ethyl acetate and satd NaHCO$_3$ solution. The aqueous phase separated off is extracted twice with ethyl acetate; the organic phases are washed with satd NaHCO$_3$ solution, 4 times with water and brine, dried over Na$_2$SO$_4$ and evaporated. Column chromatography (SiO$_2$, CH$_2$Cl$_2$/methanol= 7:2) and stirring in diethyl ether yields 4-(3-chloroanilino)-6-[(4-methylpiperazin-1-yl)methyl]-7H-pyrrolo[2,3-d] pyrimidine; HPLC: $t_{Ret}$(Grad$_{20}$)=7.4; TLC-$R_f$=0.16 (CH$_2$Cl$_2$/methanol=7:3); FAB-MS: (M+H)$^+$=357.

The starting material is obtained as follows:

Stage 1.1: At 0–5° C., 56.0 g (0.43 mol) of ethyl 2-amidinoacetate [for preparation see: *Liebigs Ann. Chem.*, 1561 (1981)] are initially introduced into 172 ml of 1,3-dimethyl-3,4,5,6-tetrahydro-2(1H)-pyrimidinone. 56.0 ml (0.45 mol) of ethyl bromopyruvate are added dropwise in the course of 30 min and the mixture is then warmed to 60° C.

for 3 h. The dark-brown reaction solution is poured onto 1 liter of ice water and extracted with 1 liter of ethyl acetate and twice with 0.5 liter of ethyl acetate each time. The organic phases are washed 3 times with 0.5 liter of water and 0.5 liter of brine, dried ($Na_2SO_4$) and evaporated. Column chromatography ($SiO_2$, hexane/ethyl acetate [1:1]) and crystallization from diethyl ether-hexane yields 2-amino-3,5-bis (ethoxycarbonyl)-1H-pyrrole; m.p. 147–149° C.; MS: $(M)^+$=226.

Stage 1.2: With the exclusion of air, 51.5 g (227 mmol) of 2-amino-3,5-bis(ethoxycarbonyl)-1H-pyrrole, 455 mmol of formamide, 227 ml of DMF and 113 ml of formic acid are stirred at 140° C. for 27 h. The resulting yellow suspension is cooled to 0–5° C. Filtering and washing with isopropanol and hexane leads to 6-ethoxycarbonyl-4-hydroxy-7H-pyrrolo[2,3-d]pyrimidine; $^1$H-NMR (DMSO-$d_6$): 13–12 (2 HX), 7.99 and 7.11 (2s, 2H), 4.31 (q, J=7, 2H), 1.32 (t, J=7, 3H).

Stage 1.3: Under a $N_2$ atmosphere, 32.0 g (154 mmol) of 6-ethoxycarbonyl-4-hydroxy-7H-pyrrolo[2,3-d]pyrimidine are suspended in 308 ml (338 mmol) of $POCl_3$ at RT and warmed to 120° C. with stirring; the solid dissolves in the course of this. After stirring at 120° C. for 3 h, the excess $POCl_3$ is distilled off (65° C. external temperature; 15 mbar). Suspension of the residue in 50 ml of ice-cold toluene, filtration and washing with toluene yields 4-chloro-6-ethoxycarbonyl-7H-pyrrolo[2,3-d]pyrimidine; m.p. 219–221° C.; $^1$H-NMR (DMSO-$d_6$) 8.77 and 7.24 (2s, 2H), 4.39 (q, J=7, 2H), 1.36 (t, J=7, 3H). Further product can be obtained from the evaporated filtrate by stirring in ethyl acetate/water.

Stage 1.4: Under a argon atmosphere, 29.0 g (128 mmol) of 4-chloro-6-ethoxy-carbonyl-7H-pyrrolo[2,3-d] pyrimidine and 18.0 ml (171 mmol) of 3-chloroaniline in 430 ml of n-butanol are stirred at 100° C. for 3 h (almost dissolved after≈1 h, then a thick suspension is formed). 400 ml of isopropanol/hexane (1:1) are then added to the reaction mixture cooled to≈50° C., and the product is filtered off and washed with isopropanol and hexane. Stirring in diethyl ether yields 4-(3-chloroanilino)-6-ethoxy-carbonyl-7H-pyrrolo[2,3-d]pyrimidine; $^1$H-NMR (DMSO-$d_6$) 13.0 and 10.53 (2 sb, 2HN), 8.48 (s, 1H), 8.13 (m, 1H), 7.78 (dm, J=8, 1H), 7.76 (s, 1H), 7.45 (t, J=8, 1H), 7.21 (dm, J=8), 1H), 4.37 (q, J=7, 2H), 1.37 (t, J=7, 3H).

Stage 1.5: Under a $N_2$ atmosphere, 1.4 g (37 mmol) of lithium aluminum hydride are added in portions to 5.70 g (18 mmol) of 4-(3-chloroanilino)-6-ethoxycarbonyl-7H-pyrrolo[2,3-d]pyrimidine. After stirring at 50° C. for 2 h, 100 ml of water are added dropwise to the reaction mixture and it is filtered through Celite. Water is added to the filtrate and the mixture is extracted 3 times with ethyl acetate. The organic phases are washed 3 times with water and brine, dried ($MgSO_4$) and evaporated. Recrystallization from isopropanol yields 4-(3-chloroanilino)-6-hydroxymethyl-7H-pyrrolo[2,3-d]pyrimidine; HPLC: $t_{Ret}(Grad_{20})$=8.2; TLC-$R_f$=0.11 ($CH_2Cl_2$/methanol [10:1]); MS: $(M)^+$=274.

Stage 1.6: With ice-cooling, 1.9 g of manganese dioxide (85%) are added to a suspension of 715 mg (2.6 mmol) of 4-(3-chloroanilino)-6-hydroxymethyl-7H-pyrrolo[2,3-d] pyrimidine in 170 ml of methylene chloride and the mixture is stirred at RT for 20 h. 20 ml of 1,3-dimethyl-3,4,5,6-tetrahydro-2(1H)-pyrimidinone (DMPU) are then added to the reaction mixture, and it is stirred for 1 h and then filtered through Hyflo. The filtration residue is again stirred (1 h) in 50 ml of methylene chloride/DMPU (1:1) and again filtered. The two filtrates are combined, evaporated and taken up in ethyl acetate/THF and water. The aqueous phases are extracted twice with ethyl acetate; the organic phases are washed 4 times with water and brine, dried ($MgSO_4$) and evaporated down to a residual volume of ≈20 ml. Addition of diethyl ether and filtration yields 4-(3-chloroanilino)-6-formyl-7H-pyrrolo[2,3-d]pyrimidine; HPLC: $t_{Ret}(Grad_{20})$= 10.1; TLC-$R_f$=0.24 ($CH_2Cl_2$/methanol [10:1]).

EXAMPLE 2

109 mg (0.40 mmol) of 4-(3-chloroanilino)-6-formyl-7H-pyrrolo[2,3-d]pyrimidine (stage 1.6) and 70 µl (0.8 mmol) of morpholine in 6 ml of methanol, 2 ml of DMPU and 50 µl of acetic acid are heated at 50° C. for 2 h. 30 mg of Raney nickel are then added and the mixture is hydrogenated at 50° C. The catalyst is filtered off, the filtrate is evaporated and the residue is dissolved in ethyl acetate and satd $Na_2CO_3$ solution. The aqueous phase separated off is extracted twice with ethyl acetate; the organic phases are washed with satd $NaHCO_3$ solution, twice with water and brine, dried ($MgSO_4$) and evaporated. The residue is taken up in methanol, and the solution is treated with silica gel and dried. The powder is added to a silica gel column and eluted with $CH_2Cl2$/methanol=10:1. Crystallization from ethyl acetate/diethyl ether/hexane yields 4-(3-chloroanilino)-6-[(morpholin-4-yl)-methyl]-7H-pyrrolo[2,3-d]pyrimidine; m.p: 244–246° C.; HPLC: $t_{Ret}(Grad_{20})$=7.4; TLC-$R_f$=0.20 ($CH_2Cl_2$/methanol 10:1); FAB-MS: $(M+H)^+$=344.

EXAMPLE 3

109 mg (0.40 mmol) of 4-(3-chloroanilino)-6-formyl-7H-pyrrolo[2,3-d]pyrimidine (stage 1.6) and 84 mg (0.8 mmol) of diethanolamine in 6 ml of ethanol, 60 drops of DMPU and 50 µl of acetic acid are stirred at RT for a few hours. 30 mg of Raney nickel are then added and the mixture is hydrogenated at 50° C. The catalyst is filtered off and the filtrate is evaporated. Column chromatography ($SiO_2$, $CH_2Cl_2$/methanol=10:1) and crystallization from ethyl acetate/diethyl ether yields 4-(3-chloroanilino)-6-[bis(2-hydroxyethyl)aminomethyl]-7H-pyrrolo[2,3-d]pyrimidine; HPLC: $t_{Ret}(Grad_{20})$=7.0; TLC-$R_f$=0.1 ($CH_2Cl_2$/methanol= 10:1); FAB-MS: $(M+H)^+$=362.

EXAMPLE 4

273 mg (1.00 mmol) of 4-(3-chloroanilino)-6-formyl-7H-pyrrolo[2,3-d]pyrimidine (stage 1.6) and 156 ml (1.2 mmol) of 4-methoxybenzylamine in 10 ml of methanol, DMPU and 126 µl (2.2 mmol) of acetic acid are stirred at RT for 1 h. 0.1 g of Raney nickel is then added and the mixture is hydrogenated at RT and finally at 50° C. The catalyst is filtered off, the filtrate is evaporated and the residue is dissolved in ethyl acetate and satd $Na_2CO_3$ solution. The aqueous phase separated off is extracted twice with ethyl acetate; the organic phases are washed with satd $NaHCO_3$ solution, and twice with water and brine, dried ($MgSO_4$) and evaporated. Stirring the residue in diethyl ether yields 4-(3-chloroanilino)-6-[(4-methoxybenzylamino)-methyl]-7H-pyrrolo[2,3-d] pyrimidine; HPLC: $t_{Ret}(Grad_{20})$=9.5; TLC-$R_f$=0.17 ($CH_2Cl_2$/methanol=10:1); FAB-MS: $(M+H)^+$=394.

EXAMPLE 5

Under an $N_2$ atmosphere, 29 µl (0.3 mmol) of boron tribromide in 2 ml of methylene chloride are added to an ice-cooled suspension of 98.5 mg (0.25 mmol) of 4-(3-chloroanilino)-6-[(4-methoxy-benzylamino)-methyl]-7H-pyrrolol[2,3-d]pyrimidine (see Example 4) in 5 ml of abs. methylene chloride. After 3 h, a further 60 µl of boron tribromide are added and the mixture is stirred at RT overnight. The reaction mixture is poured onto ice water and extracted 3 times with ethyl acetate. The organic phases are washed with satd NaHCO$_3$ solution, twice with water and brine, dried (MgSO$_4$) and evaporated. Stirring in hot isopropanol affords 4-(3-chloroanilino)-6-[(4-hydroxybenzylamino)methyl]-7H-pyrrolo[2,3-d]pyrimidine; HPLC: $t_{Ret}$(Grad$_{20}$)=8.4; FAB-MS: (M+H)$^+$=380.

EXAMPLE 6

115 mg (1.66 mmol) of hydroxylammonium chloride and 139 mg (1.69 mmol) of sodium acetate in 2 ml of water are added to 273 mg (1.00 mmol) of 4-(3-chloroanilino)-6-formyl-7H-pyrrolo[2,3-d]pyrimidine (stage1.6) in 3 ml of methanol. The suspension is heated to boiling for 3 h, cooled and filtered, and the residue is washed with water/isopropanol=1:1. The crude product is dissolved in about 80 ml of hot THF and clarified with active carbon. 10 ml of isopropanol are added to the filtrate and it is partially evaporated. The crystals formed in this process are filtered off and washed with DIPE and hexane, whereupon pure (E)-4-(3-chloroanilino)-7H-pyrrolo-[2,3-d]pyrimidine-6-carbaldehyde oxime is obtained; $^1$H-NMR (DMSO-d$_6$): 12.16 and 11.35 (2s, 2HN), 9.60 (s, 1H), 8.35 (s, 1H), 8.19 (sb, 1H), 8.17 (s, 1H), 7.79 (db, J=8, 1H), 7.35 (t, J=8, 1H), 7.05 (db, J=8, 1H), 7.03 (s, 1H); HPLC: $t_{Ret}$(Grad$_{20}$)=9.5; FAB-MS: (M+H)$^-$288.

After addition of diethyl ether and allowing to stand at −20° C., (Z)-4-(3-chloroanilino)-7H-pyrrolo[2,3-d]pyrimidine-6-carbaldehyde oxime crystallizes from the evaporated mother liquor as a mixture with ≈10% of the (E) isomer: $^1$H-NMR (DMSO-d$_6$): 12.00 (s, 2HN), 9.71 (s, 1H), 8.39 (s, 1H), 8.24 (sb, 1H), 7.84 (db, J=8, 1H), 7.67 (s, 1H), 7.52 (s, 1H), 7.35 (t, J=8, 1H), 7.05 (db, J=8, 1H); HPLC: $t_{Ret}$(Grad$_{20}$)=9.1; FAB-MS: (M+H)$^+$=288.

EXAMPLE 7

69.3 mg (0.83 mmol) of O-methylhydroxylamine hydrochloride and 69.3 mg (0.845 mmol) of sodium acetate in 1 ml of water are added to 163.3 mg (0.5 mmol) of 4-(3-chloroanilino)-6-formyl-7H-pyrrolo[2,3-d]pyrimidine (stage1.6) in 1 ml of methanol. The suspension is heated to boiling for 4 h, cooled and filtered, and the residue is washed with water/isopropanol and finally diethyl ether. 4-(3-Chloroanilino)-7H-pyrrolo[2,3-d]pyrimidine-6-carbaldehyde O-methyl oxime is obtained; HPLC: $t_{Ret}$(Grad$_{20}$)=11.3; TLC-R$_f$=0.31 (CH$_2$Cl$_2$/methanol 10:1) FAB-MS: (M+H)$^+$=302.

EXAMPLE 8

168.5 mg (0.53 mmol) of 4-(3-chloroanilino)-6-ethoxycarbonyl-7H-pyrrolo[2,3-d]pyrimidine (stage1.4) in 3 ml of morpholine are stirred at 50° C. for 5 days and at 100° C. for 1 day. Silica gel is added to the reaction mixture, it is evaporated, and the resulting powder is applied to a silica gel column and eluted with ethanol/methylene chloride 1:15. Stirring the reaction product in isopropanol leads to 4-(3-chloroanilino)-6-(morpholin-4-yl-carbonyl)-7H-pyrrolo[2,3-d]pyrimidine; HPLC: $t_{Ret}$(Grad$_{20}$)=9.2; TLC-R$_f$=0.56 (CH$_2$Cl$_2$/methanol=10:1); MS: (M)$^+$=357.

EXAMPLE 9

98 mg (0.33 mmol) of TPTU, followed by 133 μl (1.2 mmol) of N-methyl-piperazine in 1 ml of DMF (→solution) are added to a suspension of 97.6 mg (0.30 mmol) of 6-carboxy-4-(3-chloroanilino)-7H-pyrrolo[2,3-d]pyrimidine in 7 ml of DMF. After 1 h, a further 30 mg of TPTU are added and the mixture is stirred overnight at RT. The reaction mixture is evaporated in a HV, and the residue is treated with ethanol/methylene chloride (1:2) and finally with about 4 ml of ethanol/water (3:1). 4-(3-chloroanilino)-6-[(4-methylpiperazin-1-yl)carbonyl]-7H-pyrrolo[2,3-d]pyrimidine crystallizes in this process and is filtered off and washed with ethanol/water (1:1) and isopropanol/hexane (1:1); m.p. 276–278° C.; HPLC: $t_{Ret}$(Grad$_{20}$)=7.3; TLC-R$_f$=0.21 (CH$_2$Cl$_2$/ethanol=2:1); MS: (M)$^+$=370.

The starting material is obtained as follows:

Step 9.1: A solution of 25 mg (0.6 mmol) of LiOH.H$_2$O in 0.4 ml of H$_2$O is added dropwise to a suspension of 95 mg (0.30 mmol) of 4-(3-chloroanilino)-6-ethoxy-carbonyl-7H-pyrrolo[2,3-d]pyrimidine (see stage1.4) in 0.7 ml of methanol and the mixture is heated to boiling for 4.5 h. It is cooled in an ice bath and acidified with 0.6 ml of 1 normal HCl solution. Filtering off and washing with water yields 6-carboxy-4-(3-chloroanilino)-7H-pyrrolo[2,3-d]pyrimidine; HPLC: $t_{Ret}$(Grad$_{20}$)=8.7; FAB-MS: (M+H)$^+$=289.

EXAMPLE 10

144 mg (0.50 mmol) of 6-aminocarbonyl-4-(3-chloroanilino)-7H-pyrrolo[2,3-d]pyrimidine and 202 mg (0.5 mmol) of Lawesson's reagent in 5 ml of THF are heated to boiling for 17 h and the mixture is then evaporated. Column chromatography (SiO$_2$, CH$_2$Cl$_2$/ethanol=15:1) of the residue and stirring in diethyl ether yields 4-(3-chloroanilino)-6-(thiocarbamoyl)-7H-pyrrolo[2,3-d]pyrimidine; HPLC: $t_{Ret}$(Grad$_{20}$)=9.8; TLC-R$_f$=0.44 (CH$_2$Cl$_2$/methanol=10:1); FAB-MS: (M+H)$^+$=304; IR: (KBr) inter alia 1614s, 1566s, 1506m, 1474s, 1380m, 1354m, 1294m, 1134m.

The starting material is obtained as follows:

Stage 10.1: 90 mg (0.285 mmol) of 4-(3-chloroanilino)-6-ethoxycarbonyl-7H-pyrrolo-[2,3-d]pyrimidine (stage 1.4) in 30 ml of methanol and≈5 g of ammonia are heated at 120° C. for 48 h in an autoclave. The reaction mixture is treated with silica gel, evaporated, applied to a silica gel column as a powder and finally eluted with methylene chloride/methanol/THF (210:35:10). Filtration with methanol through an alumina column (basic) and stirring in ethyl acetate yields 6-aminocarbonyl-4-(3-chloroanilino)-7H-pyrrolo[2,3-d]pyrimidine; HPLC: $t_{Ret}$(Grad$_{20}$)=8.1; TLC-R$_f$=0.18 (CH$_2$Cl$_2$/methanol [10:1]); high resolution MS: (M+H)$^+$=288.0669 (calc. 288.0652).

The starting material is obtained alternatively and advantageously as follows:

Alternative stage 10.1: A mixture of 2.165 g (7.5 mmol) of 6-carboxy-4-(3-chloroanilino)-7H-pyrrolo[2,3-d]pyrimidine in 60 ml of THF and 10 ml of DMPU is heated under reflux for 30 min and then cooled to 0° C., whereupon a fine suspension is obtained. 824 μl (7.5 mmol) of N-methylmorpholine followed by 981 μl (7.5 mmol of isobutyl chloroformate in 10 ml of THF and, after 1 h at 0° C., 824 μl (7.5 mmol) of N-methylmorpholine followed by 981 μl (7.5 mmol) of isobutyl chloroformate again are added dropwise. The mixture is stirred for 1 h and then added dropwise to 70 ml of a saturated solution of ammonia in dioxane. After 3 h, the mixture is concentrated in vacuo. The residue is poured into water, and the precipitate is filtered off and washed with water and boiling isopropanol, whereupon 6-aminocarbonyl-4-(3-chloroanilino)-7H-pyrrolo[2,3-d]pyrimidine is obtained. Further product is obtained from the isopropanol filtrate.

EXAMPLE 11

57.5 mg (0.19 mmol) of 4-(3-chloroanilino)-6-(thiocarbamoyl)-7H-pyrrolo[2,3-d]pyrimidine (see Example 10) in 3 ml of methanol and 57.3 mg (0.25 mmol) of 4-methoxyphenacyl bromide are heated to boiling for 17 h. Cooling of the pale yellow suspension, filtering and washing with isopropanol/diethyl ether yields 4-(3-chloroanilino)-6-[4-(4-methoxyphenyl)thiazol-2-yl]-7H-pyrrolo[2,3-d]pyrimidine; HPLC: $t_{Ret}(Grad_{20})$=15.4; TLC-$R_f$=0.33 ($CH_2Cl_2$/methanol=10:1); FAB-MS: $(M+H)^+$=434.

EXAMPLE 12

57.5 mg (0.19 mmol) of 4-(3-chloroanilino)-6-(thiocarbamoyl)-7H-pyrrolo[2,3-d]pyrimidine (see Example 10) and 34 ml of 1-bromo-2-butanone (Aldrich; Milwaukee/USA) in 3 ml of dioxane are heated to boiling for 2 h. Cooling, filtering the suspension and washing with isopropanol/diethyl ether yields 4-(3-chloroanilino)-6-(4-ethylthiazol-2-yl)-7H-pyrrolo[2,3-d]pyrimidine; HPLC: $t_{Ret}(Grad_{20})$=13.6; FAB-MS: $(M+H)^+$=356.

EXAMPLE 13

4-(3-Chloroanilino)-6-(4,5-dimethylthiazol-2-yl)-7H-pyrrolo[2,3-d]pyrimidine is obtained by the process described in this text.

EXAMPLE 14

19 mg (0.45 mmol) of lithium chloride and 19.5 mg (0.30 mmol) of sodium azide are added to a solution of 80.9 mg (0.30 mmol) of 4-(3-chloroanilino)-6-cyano-7H-pyrrolo[2,3-d]pyrimidine in 1 ml of methoxyethanol and the mixture is heated to boiling for 6.5 h. The cooled reaction mixture is poured onto water/HCl (conc.) 10:1, the mixture is stirred for 30 min, and the solid is filtered off and washed with water. Dissolving the crystals in THF/isopropanol, partial evaporation to crystallization, filtering off and washing with diethyl ether affords 4-(3-chloroanilino)-6-(tetrazol-5-yl)-7H-pyrrolo[2,3-d]pyrimidine; HPLC: $t_{Ret}(Grad_{20})$=9.5; TLC-$R_f$=0.45 ($CH_2Cl_2$/methanol=7:1); FAB-MS: $(M+H)^+$=313.

The starting material is obtained as follows:

Stage 14.1: 13 ml of phosphorus oxychloride are added to 1.048 g (3.6 mmol) of 6-aminocarbonyl-4-(3-chloroanilino)-7H-pyrrolo[2,3-d]pyrimidine (see Stage 10.1) and 0.7 ml of N,N-dimethylacetamide. After stirring at RT for 1 h and at 100° C. for 4 h, the reaction mixture is poured into an ice-cooled saturated solution of $NaHCO_3$. Extraction with ethyl acetate (3 times), washing the organic layers with saturated $NaHCO_3$ solution, water and saturated sodium chloride solution, drying ($Na_2SO_4$) and concentrating leads to a solid. Column chromatography ($SiO_2$; ethyl acetate), and stirring the crude product in diethyl ether and hexane yields 4-(3-chloroanilino)-6-cyano-7H-pyrrolo[2,3-d]pyrimidine; m.p. 284–287° C.; TLC-$R_f$=0.71 ($CH_2Cl_2$/methanol [10:1]);HPLC: $t_{Ret}(Grad_{20})$=11.8.

EXAMPLE 15

50.4 mg (0.60 mmol) of $NaHCO_3$ and, at 0–5° C., 600 µl (0.60 mmol) of methyl iodide (1 M in dioxane) are added to 187.6 mg (0.60 mmol) of 4-(3-chloroanilino)-6-(tetrazol-5-yl)-7H-pyrrolo[2,3-d]pyrimidine (see Example 14) in 12 ml of DMF. After stirring at RT for 18 h, the mixture is diluted with ethyl acetate, a little THF and water, and the aqueous phase is separated off and extracted again with ethyl acetate and a little THF. The organic phases are washed twice with water and brine, dried with $MgSO_4$ and evaporated. Stirring the residue in THF/ethanol affords a 2:1 mixture of 4-(3-chloroanilino)-6-(2-methyltetrazol-5-yl)-7H-pyrrolo[2,3-d]pyrimidine and 4-(3-chloroanilino)-6-(1-methyltetrazol-5-yl)-7H-pyrrolo[2,3-d]pyrimidine; HPLC: $t_{Ret}(Grad_{20})$=10.5 (1 part) and 10.7 (2 parts),$^1$H-NMR (DMSO-$d_6$) inter alia 4.45 (s, 2-$H_3$C-tetrazole), 4.32 (s, 1-$H_3$C-tetrazole); FAB-MS: $(M+H)^+$=327.

EXAMPLE 16

0.1 g (0.304 mmol) of (R)-6-(4-aminophenyl)-4-[(1-phneylethyl)amino]-7H-pyrrolo[2,3-d]pyrimidine and 0.026 ml (0.33 mmol) of methanesulfochloride in 1 ml of abs. dimethylacetamide are stirred at 0° C. for 4 h until starting material is no longer present in the TLC. The reaction mixture is poured onto 10 ml of ice water. It is extracted with ethyl acetate and 20 ml of an aqueous $NaHCO_3$ solution. The organic phase is washed with water, dried and concentrated, (R)-6-(4-methylsulfonylaminophenyl)-4-[(1-phenylethyl)amino]-7H-pyrrolo[2,3-d]pyrimidine crystallizing out. The product is washed with hexane; m.p. 253–256° C.; FAB-MS: $(M+H)^+$=408.

The starting material is obtained as follows:

Stage 16.1: Analogously to stage 19.4, boiling 6.0 g (220 mmol) of 4-chloro-6-(4-nitrophenyl)-7H-pyrrolo[2,3-d]pyrimidine (see Stage 19.3) with 6.04 g of (R)-(+)-1-phenylethylamine in 120 ml of n-butanol gives (R)-6-(4-nitrophenyl-4-[(1-phenylethyl)amino]-7H-pyrrolo[2,3-d]pyrimidine as rust-brown crystals of m.p.>250° C.

Stage 16.2: Analogously to stage 19.5, reduction of (R)-6-(4-nitrophenyl-4-[(1-phenylethyl)amino]-7H-pyrrolo[2,3-d]pyrimidine with Raney nickel in THF/methanol gives (R)-6-(4-aminophenyl-4-[(1-phenylethyl)amino]-7H-pyrrolo[2,3-d]pyrimidine; m.p. 234–235° C.; MS: $M^+$=329.

EXAMPLE 17

Analogously to Example 16, the following are prepared from (R)-6-(4-aminophenyl)-4-[(1-phenylethyl)amino]-7H-pyrrolo[2,3-d]pyrimidine (see stage 16.2) and the appropriate alkyl sulfochloride:

a) (R)-6-(4-ethylsulfonylaminophenyl)-4-[(1-phenylethyl)amino]-7H-pyrrolo[2,3-d]pyrimidine; m.p. 260–261° C.; FAB-MS: $(M+H)^+$=422, and b) (R)-6-(4-isopropylsulfonylaminophenyl)-4-[(1-phenylethyl)amino]-7H-pyrrolo[2,3-d]-pyrimidine; m.p. 262–263° C.; FAB-MS: $(M+H)^+$=436.

EXAMPLE 18

Analogously to Example 16, the following are prepared from (R)-6-(3-aminophenyl)-4-[(1-phenylethyl)amino]-7H-pyrrolo[2,3-d]pyrimidine and the appropriate alkyl sulfochloride:

a) (R)-6-(3-methylsulfonylaminophenyl)-4-[(1-phenylethyl)amino]-7H-pyrrolo[2,3-d]pyrimidine; m.p. 139–148° C. (amorphous); MS: $(M^+)$=407, b) (R)-6-(3-ethylsulfonylaminophenyl)-4-[(1-phenylethyl)amino]-7H-pyrrolo[2,3-d]pyrimidine; m.p. 235–236° C.; FAB-MS: $(M+H)^+$=422, and c) (R)-6-(3-isopropylsulfonylaminophenyl)-4-[(1-phenylethyl)amino]-7H-pyrrolo[2,3-d]pyrimidine; m.p. 257–258° C.; FAB-MS: $(M+H)^+$=436.

The starting material is obtained as follows:

Stage 18.1: Analogously to the method described in stage 19.4, boiling 20.0 g (700 mmol) of 4-chloro-6-(3- nitrophenyl)-7H-pyrrolo[2,3-d]pyrimidine (prepared analogously to stages 19.1 to 19.3) with 23.1 ml (168 mmol) of (R)-phenylethylamine in 23.1 ml of n-butanol gives (R)-6-(3-nitrophenyl)-4-[(1-phenylethyl)amino]-7H-pyrrolo-[2,3-d]pyrimidine as rust-brown crystals of m.p.>250° C.; MS: M⁺=359.

Stage 18.2: Analogously to stage 19.5, reduction of (R)-6-(3-nitrophenyl-4-[(1-phenylethyl)amino]-7H-pyrrolo[2,3-d]pyrimidine with Raney nickel in THF/methanol gives (R)-6-(3-aminophenyl)-4-[(1-phenylethyl)amino]-7H-pyrrolo[2,3-d]pyrimidine; m.p. 129–190° C. (amorphous); MS: M⁺=329.

EXAMPLE 19

Analogously to Example 16, the following are prepared from 6-(4-aminophenyl)-4-(3-chloroanilino)-7H-pyrrolo[2,3-d]pyrimidine and the corresponding alkyl sulfochloride:

a) 6-(4-methylsulfonylaminophenyl)-4-(3-chloroanilino)-7H-pyrrolo[2,3-d]pyrimidine; m.p.>300° C.; FAB-MS: (M+H)⁺=414, b) 4-(3-chloroanilino)-6-(4-ethylsulfonylaminophenyl)-7H-pyrrolo[2,3-d]pyrimidine; m.p.>300° C.; FAB-MS: (M+H)⁺=428, c) 4-(3-chloroanilino)-6-(4-isopropylsulfonylaminophenyl)-7H-pyrrolo[2,3-d]pyrimidine; m.p.>300° C.; FAB-MS: (M+H)⁺=442 and d) 4-(3-chloroanilino)-6-(4-phenylsulfonylaminophenyl)-7H-pyrrolo[2,3-d]pyrimidine; m.p.>300° C.; FAB-MS: (M+H)⁺=475.

The starting material is obtained as follows:

Stage 19.1: In a dry three-necked flask, 75 ml of abs. ethanol and 6.5 g (390 mmol) of ethyl 2-amidinoacetate hydrochloride [for preparation see: Liebigs Ann. Chem., 1895 (1977)] are initially introduced under argon, and the mixture is cooled to 0–5° C. and treated with 2.65 g (390 mmol) of sodium ethoxide. 5 g (195 mmol) of 2-bromo-1-(4-nitrophenyl)ethan-1-one are then added, and the mixture is allowed to come to RT and is stirred further for 48 h. The reaction mixture is then partitioned between water and ethyl acetate. The ethyl acetate phase is washed three times with water and once with satd NaCl solution, dried and filtered, and the filtrate is evaporated. The red-brown residue is suspended in hexane, 2-amino-3-ethoxycarbonyl-5-(4-nitrophenyl)pyrrole precipitating as a crude product (purity 93%) which is used for the next stage without further purification; MS: (M)⁺=275.

Stage 19.2: 2.5 g (97 mmol) of 2-amino-3-ethoxycarbonyl-5-(4-nitrophenyl)pyrrole, 19.4 ml of formamide, 9.7 ml of DMF and 3.1 ml of formic acid are stirred at 150° C. together for 22 h. 1 ml of isopropanol is added to the warm reaction mixture. After cooling the reaction mixture, the precipitated product is filtered off. It is washed successively three times with 10 ml of ethanol each time, twice with 10 ml of isopropanol each time and twice with 10 ml of hexane each time. 4-Hydroxy-6-(4-nitrophenyl)-7H-pyrrolo[2,3-d]pyrimidine is obtained as rust-brown crystals which are employed for the next stage; MS: (M)⁺=256.

Stage 19.3: By heating 4-hydroxy-6-(4-nitrophenyl)-7H-pyrrolo[2,3-d]pyrimidine with POCl₃, 4-chloro-6-(4-nitrophenyl)-7H-pyrrolo[2,3-d]pyrimidine is prepared (purity 93%); m.p.>280° C.; FAB-MS: (M+H)⁺=275.

Stage 19.4: By boiling 0.25 g (0.91 mmol) of 4-chloro-6-(4-nitrophenyl)-7H-pyrrolo-[2,3-d]pyrimidine with 0.19 ml of 3-chloroaniline in 5 ml of n-butanol, 4-(3-chloroanilino)-6-4-nitrophenyl)-7H-pyrrolo[2,3-d]pyrimidine is obtained as rust-brown crystals; m.p.>250° C.; ¹H-NMR (360 Mhz, DMSO-d₆): 12.95 (s, pyrrole-NH), 10.3 (s, aniline-NH), 8.45 (s, pyrimidine-H), 8.24 (s, aromatic H), 7.18–8.4 (7 aromatic H+pyrrole-5H); MS: (M)⁺=365.

Stage 19.5: 150 mg (0.41 mmol) of 4-(3-chloroanilino)-6-(4-nitrophenyl)-7H-pyrrolo-[2,3-d]pyrimidine are hydrogenated with 50 mg of Raney nickel in 20 ml of THF/methanol at RT and normal pressure for 5 h, the desired product precipitating in the course of this. The catalyst is filtered off and the filter residue is washed with warm THF. The filtrate is evaporated to dryness. The crude product is purified by digesting several times in methanol and precipitating from THF/hexane, whereupon 6-(4-aminophenyl)-4-(3-chloroanilino)7H-pyrrolo[2,3-d]pyrimidine is obtained as pale beige crystals; m.p.>290° C.; ¹H-NMR (360 MHz, DMSO-d₆): 12.05 (s, pyrrole-NH), 9.38 (s, aniline-NH), 8.31 (s, pyrimidine-H), 8.24 (s, aromatic H), 7.80 (d, aromatic H), 7.53 (d, 2 aromatic H), 7.35 (t, aromatic H), 7.05 (d, aromatic H), 6.90 (s, pyrrole-5H), 6.64 (d, 2 aromatic H), 5.35 (s, NH2); MS: (M)⁺=335.

EXAMPLE 20

Analogously to Example 16, the following are prepared from 6-(3-aminophenyl)-4-(3-chloroanilino)-7H-pyrrolo[2,3-d]pyrimidine and the corresponding alkyl sulfochloride:

a) 4-(3-chloroanilino)-6-(3-methylsulfonylaminophenyi)-7H-pyrrolo[2,3-d]pyrimidine; m.p.>300° C.; FAB-MS: (M+H)⁺=414, b) 4-(3-chloroanilino)-6-(3-ethylsulfonylaminophenyl)-7H-pyrrolo[2,3-d]pyrimidine; m.p. 228–230° C.; FAB-MS: (M+H)⁺=428, and c) 4-(3-chloroanilino)-6-(3-isopropylsulfonylaminophenyl)-7H-pyrrolo[2,3-d]pyrimidine; m.p. 233° C.; FAB-MS: (M+H)⁺=442.

The starting material is obtained as follows:

Stage 20.1: Analogously to stage 19.4, boiling 2.0 g (7.28 mmol) of 4-chloro-6-(3-nitrophenyl)-7H-pyrrolo[2,3-d]pyrimidine with 4.2 ml (40 mmol) of 3-chloroaniline in 150 ml of n-butanol gives 6-(3-nitrophenyl)-4-(3-chloroanilino)-7H-pyrrolo[2,3-d]pyrimidine as yellowish crystals of m.p.>250° C.; MS: M⁺=365.

Stage 20.2: Analogously to stage 19.5, reduction of 6-(3-nitrophenyl)-4-(3-chloroanilino)-7H-pyrrolo[2,3-d]pyrimidine with Raney nickel in THF/methanol gives 6-(3-aminophenyl)-4-(3-chloroanilino)-7H-pyrrolo[2,3-d]pyrimidine; m.p. 293–295° C.; MS: M⁺–336.

EXAMPLE 21

0.2 g (0.56 mmol) of 6-(4-aminophenyl)-4-(3-chloroanilino)-7H-pyrrolo[2,3-d]pyrimidine (see stage 19.5), 0.097 ml (0.67 mmol) of N,N-dimethylformamide dimethyl acetal and 0.112 ml (0.73 mmol) of triethylamine are stirred at RT for 24 h in 10 ml of THF until all the starting material has disappeared in the TLC. The reaction solution is concentrated to dryness in vacuo and the residue is chromatographed on a silica gel column. Crystallization from THF/hexane or ethyl acetate/hexane gives 4-(3-chloroanilino)-6-(4-[dimethylamino-methylenamino]phenyl)-7H-pyrrolo[2,3-d]pyrimidine; m.p.>300° C.; MS: (M)⁺=390.

EXAMPLE 22

Analogously to Example 21, the following compounds are prepared from 6-(4-aminophenyl)-4-(3-chloroanilino)-7H-pyrrolo[2,3-d]pyrimidine (see stage 19.5) and the corresponding N,N-dialkylformamide dimethyl acetal or heterocyclyl aldehyde dimethyl acetal:

a) 4-(3-chloroanilino)-6-(4-diethylaminomethylenamino]phenyl)-[7H-pyrrolo[2,3-d]pyrimidine; m.p.>310° C.; FAB-MS: (M+H)$^+$=419, b) 4-(3-chloroanilino)-6-(4-[piperidinomethylenaminophenyl)-7H-pyrrolo[2,3-d]pyrimidine; m.p.>300° C.; MS: (M)$^+$=430, c) 4-(3-chloroanilino)-6-(4-[morpholinomethylenamino]phenyl)-7H-pyrrolo[2,3-d]pyrimidine; m.p.>310° C.; MS: (M)$^+$=432, and d) 4-(3-chloroanilino)-6-{4-[(4-methylpiperazino)methylenamino]phenyl}-7H-pyrrolo[2,3-d]pyrimidine; m.p.>310° C.; FAB-MS: (M+H)$^+$=446.

EXAMPLE 23

Analogously to Example 21, the following compounds are prepared from 6-(3-aminophenyl)-4-(3-chloroanilino)-7H-pyrrolo[2,3-d]pyrimidine (see stage 20.2) and the corresponding N,N-dialkylformamide dimethyl acetal or morpholinoaldehyde dimethyl acetal:

a) 4-(3-chloroanilino)-6-(3-[dimethylaminomethylenamino]phenyl)-7H-pyrrolo[2,3-d]pyrimidine; m.p. 266–268° C.; MS: (M)$^+$=390, b) 4-(3-chloroanilino)-6-(3-[diethylaminomethylenamino]-phenyl)-7H-pyrrolo[2,3-d]pyrimidine; m.p. 171–172° C.; FAB-MS: (M+H)$^+$= 419, and c) 4-(3-chloroanilino)-6-(3-[morpholinomethylenamino]phenyl)-7H-pyrrolo[2,3-d]pyrimidine; m.p. 284–286° C.; FAB-MS: (M+H)$^+$=433.

EXAMPLE 24

Analogously to Example 21, the following compound is prepared from (R)-6-(4-aminophenyl)-4-[(1-phenylethyl)amino]-7H-pyrrolo[2,3-d]pyrimidine (see stage 16.2) and N,N-dimethylformamide dimethyl acetal:

(R)-6-(4-[dimethylaminomethylenamino]phenyl)-4-[(1-phenylethyl)amino]-7H-pyrrolo[2,3-d]pyrimidine; m.p.>300° C.; MS: (M+H)$^+$=385.

EXAMPLE 25

Analogously to Example 21, the following compound is prepared from (R)-6-(3-aminophenyl)-4-[(1-phenylethyl)amino]-7H-pyrrolo[2,3-d]pyrimidine (see stage 18.2) and N,N-dimethylformamide dimethyl acetal:

(R)-6-(3-[dimethylaminomethylenamino]phenyl)-4-[(1-phenylethyl)amino]-7H-pyrrolo[2,3-d]pyrimidine; m.p. 267–269° C.; FAB-MS: (M+H)$^+$=385.

EXAMPLE 26

738 mg (2.02 mmol) of 6-(4-carbonylphenyl)-4-(3-chloroanilino)-7H-pyrrolo[2,3-d]pyrimidine are stirred at room temperature for 3 h with 3 equivalents of morpholine and 3.5 equivalents of DEPC (Aldrich) in DMF. The reaction solution is poured onto water and the solid is filtered off and washed with water and methanol. The product obtained is chromatographed on silica gel and eluted with chloroform/methanol/acetic acid/water (850:130:15:5; v/v). The product obtained is digested in diethyl ether, filtered off and dried. 4-(3-Chloroanilino-6-(4-[morpholin-4-yl-carbonyl]phenyl)-7H-pyrrolo[2,3-d]pyrimidine is obtained as beige crystals; m.p.>250° C.; FAB-MS: (M+H)$^+$=434.

EXAMPLE 27

Analogously to Example 26, starting from (3-chloroanilino)-6-(4-carbonylphenyl)-7H-pyrrolo[2,3-d]pyrimidine and N-methylpiperazine 4-(3-chloroanilino)6-(4-[4-methylpiperazin-1-yl]-carbonylphenyl)-7H-pyrrolo[2,3-d]pyrimidine is obtained; m.p. 250° C.; FAB-MS: (M+H)$^+$=447.

EXAMPLE 28

300 mg (0.89 mmol) of 6-(4-aminophenyl)-4-(3-chloroanilino)-7H-pyrrolo[2,3-d]pyrimidine (see Stage 19.5), dissolved in 20 ml of abs. THF and 2 ml (3.56 mmol) of DMA are treated with 0.29 ml of ethyl isocyanate (FLUKA) with exclusion of moisture and heated under reflux until starting material is no longer present in the TLC (24 h). The reaction mixture is evaporated to dryness in vacuo and the crude product is chromatographed on silica gel, ethyl acetate/methanol being used as the eluent. Fractions which contain the desired product are combined and evaporated to dryness. The residue is dissolved in a little THF. The target compound is precipitated/crystallized by addition of n-hexane. Colorless crystals of 4-(3-chloroanilino)-6-(4-[N$^3$-ethylureido]phenyl)-7H-pyrrolo[2,3-d]pyrimidine are obtained; m.p.>290° C., FAB-MS: (M+H)$^+$=407.

EXAMPLE 29

Analogously to Example 28, the following compounds are prepared from 6-(3-aminophenyl)-4-(3-chloroanilino)-7H-pyrrolo[2,3-d]pyrimidine (see Stage 20.2) and the corresponding alkyl isocyanate or phenyl isocyanate:

a) 4-(3-chloroanilino)-6-(3-[N$^3$-ethylureidophenyl)-7H-pyrrolo[2,3-d]pyrimidine; m.p.>300° C.; FAB-MS: (M+H)$^+$=407, and b) 4-(3-chloroanilino)-6-(3-[N$^3$-phenylureidophenyl)-7H-pyrrolo[2,3-d]pyrimidine; m.p.>300° C.; FAB-MS: (M+H)$^+$=455.

EXAMPLE 30

Analogously to Example 28, (R)-6-(4-[N$^3$-ethylureido]phenyl)-4-[(1-phenylethyl)amino]-7H-pyrrolo[2,3-d]pyrimidine is prepared from (R)-6-(4-aminophenyl)-4-[(1-phenylethyl)amino]-7H-pyrrolo[2,3-d]pyrimidine (see Stage 16 . . . ) and ethyl isocyanate; m.p. 238–240° C.; FAB-MS: (M+H)$^+$=401.

EXAMPLE 31

Analogously to Example 28, (R)-6-(3-[N$^3$-ethylureido]-phenyl)-4-[(1-phenylethyl)amino]7H-pyrrolo[2,3-d]pyrimidine is prepared from (R)-6-(3-aminophenyl)-4-[(1-phenylethyl)amino]-7H-pyrrolo[2,3-d]pyrimidine (see Stage 18.2) and ethyl isocyanate; m.p. 177–178° C.; FAB-MS: (M+H)$^+$=401.

EXAMPLE 32

Analogously to the method described in Example 28, 300 mg (0.89 mmol) of 6-(4-aminophenyl)-4-(3-chloroanilino)-7H-pyrrolo[2,3-d]pyrimidine (see Stage 19.5) dissolved in 20 ml of abs. THF and 2 ml of DMA, and 0.27 ml (3.56 mmol) of methyl isothiocyanate (EGA) yield, after recrystallization from THF-n-hexane, 4-(3-chloroanilino)-6-(4-[N$^3$-ethylthioureido]phenyl)-7H-pyrrolo[2,3-d]pyrimidine in the form of colorless crystals; m.p. 275–276° C.; FAB-MS: (M+H)$^+$=409.

EXAMPLE 33

Analogously to Example 32, 6-(3-aminophenyl)-4-(3-chloroanilino)-7H-pyrrolo[2,3-d]pyrimidine and methyl isothiocyanate yield 4-(3-chloroanilino)-6-(3-(N³-methylthioureido]phenyl)-7H-pyrrolo[2,3-d]pyrimidine: m.p. 198–200° C.; FAB-MS: (M+H)⁺=409.

EXAMPLE 34

Analogously to Example 32, (R)-6-(4-aminophenyl)-4-[(1-phenylethyl)amino]-7H-pyrrolo[2,3-d]pyrimidine (see Stage 16.2) and methyl isothiocyanate yield (R)-6-(4-[N³-methylthioureido]phenyl)-4-[(1-phenylethyl)amino]-7H-pyrrolo[2,3-d]-pyrimidine; m.p. 225–228° C.; FAB-MS: (M+H)⁺=403.

EXAMPLE 35

Analogously to Example 32, (R)-6-(3-aminophenyl)-4-[(1-phenylethyl)amino-]7H-pyrrolo[2,3-d]-pyrimidine (see Stage 18.2) and methyl isothiocyanate yield (R)-6-(3-[N³-methylthioureido]phenyl)-4-[(1-phenylethyl)amino]-7H-pyrrolo[2,3-d]pyrimidine; m.p. 188–190° C.; FAB-MS: (M+H)⁺=403.

EXAMPLE 36

300 mg (0.89 mmol) of 6-(4-aminophenyl-4-(3-chloroanilino)-7H-pyrrolo-[2,3-d]pyrimidine (see Stage 19.5), dissolved in 2.7 ml of abs. dioxane and 0.13 ml of 2,6-lutidine, are treated with a solution of 0.10 ml (0.98 mmol) of methyl chloroformate in 1.8 ml of abs. dioxane with the exclusion of moisture and stirred at RT until starting material is no longer present in the TLC. The reaction mixture is added to 50 ml of water. It is then extracted with 200 ml of ethyl acetate and 10 ml of 5% aqueous sodium hydrogencarbonate solution. The combined ethyl acetate phases are washed 3 times with water, dried and evaporated in vacuo. The residue is chromatographed on silica gel, eluting with methylene chloride and increasing amounts of methanol. The target compound, ⁴-(3-chloroanilino)-6-(4-methoxycarbonylaminophenyl)-7H-pyrrolo-[2,3-d]pyrimidine, is crystallized from methanol or acetone in the form of slightly yellow-colored crystals; m.p.>300° C.; FAB-MS: (M+H)⁺=394.

EXAMPLE 37

Analogously to Example 36, the following compounds are prepared from 6-(4-aminophenyl)-4-(3-chloroanilino)-7H-pyrrolo[2,3-d]pyrimidine (see Stage 19.5) and the corresponding alkyl chloroformate:

a) 4-(3-chloranilino)-6-(4-ethoxycarbonylaminophenyl)-7H-pyrrolo[2,3-d]pyrimidine; m.p.>300° C.; FAB-MS: (M+H)⁺=408, b) 4-(3-chloroanilino)-6-(4-isopropyloxycarbonylaminophenyl)-7H-pyrrolo[2,3-d]pyrimidine; m.p.>300° C.; FAB-MS: (M+H)⁺=422 and c) 4-(3-chloroanilino)-6-{4-[(2-methylpropyloxy)carbonylamino]phenyl}-7H-pyrrolo-[2,3-d]pyrimidine; m.p.>282–284° C.; FAB-MS: (M+H)⁺=436.

EXAMPLE 38

3.53 g (9.0 mmol) of 4-(3-chloroanilino)-6-(4-ethoxycarbonylphenyl)-7H-pyrrolo[2,3-d]pyrimidine are suspended in 150 ml of THF. At 54° C., a total of 0.845 g (21.6 mmol) of lithium aluminum hydride are introduced in the course of 5 h. For working up, 1 ml of water, 2 ml of 1N sodium hydroxide solution and 1 ml of water, followed by 10 g of sodium sulfate, are added successively. The solid is filtered off and the filtrate is concentrated. The residue obtained is washed with methanol and diethyl ether and then dried. 4-(3-Chloroanilino)-6-(4-hydroxymethlyphenyl)-7H-pyrrolo[2,3-d]pyrimidine is obtained in colorless crystals; m.p.>250° C.; FAB-MS (M+H)⁺=351.

EXAMPLE 39

The following compounds are obtained analogously to the processes described in this text:

a) (R)-6-(3-benzylaminophenyl)-4-[(1-phenylethyl)amino]-7H-pyrrolo[2,3-d]pyrimidine; m.p. 253–255° C., b) 6-(4-benzyloxy-3-methoxyphenyl)-4-(3-chloroanilino)-7H-pyrrolo[2,3-d]pyrimidine; m.p. 237–238° C., c) 6-(4-benxyloxy-3-methoxyphenyl)-4-(3-methylanilino)-7H-pyrrolo[2,3-d]pyrimidine; m.p. 231–234° C., d) 6-(4-hydroxy-3-methoxyphenyl)-4-(3-methylanilino)-7H-pyrrolo[2,3-d]pyrimidine; m.p. 234–236° C., e) 4-anilino-6-(4-hydroxy-3-methoxyphenyl)-7H-pyrrolo[2,3-d]pyrimidine hydrochloride; m.p. 242–246° C., f) 4-(3-chloroanilino)-6-(4-hydroxy-3-m ethoxyphenyl)-7H-pyrrolo[2,3-d]pyrimidine hydrochloride; m.p.>250° C., g) 4-(3-chloroanilino)-6-(4-(fur-2-yl-carbonylamino]phenyl)-7H-pyrrolo[2,3-d]pyrimidine; m.p.>300° C., h) 4-(3-chloroanilino)-6-(4-(thien-2-yl-carbonylamino]phenyl)-7H-pyrrolo[2,3-d]pyrimidine; m.p>300° C.;

i) 6-(4-benzylaminophenyl)-4-(3-chloroanilino)-7H-pyrrolo[2,3-d]pyrimidine; m.p.>300° C., j) (R)-6-(4-methoxyphenyl-4-[(1-phenylethyl)amino]-7H-pyrrolo[2,3-d]pyrimidine; m.p. 256–257° C., k) 4-(3-chloroanilino)-6-{4-[(1-dimethylamino-1-isopropylmethylen)amino}phenyl)-7H-pyrrolo[2,3-d]pyrimidine; m.p. 255–257° C., and l) 4-(3-chloroanilino)-6-(thiazol-2-yl)-7H-pyrrolo[2,3-d]pyrimidine.

EXAMPLE 40

Dry-filled Capsules 5000 capsules, each comprising as active ingredient 0.25 g of one of the compounds of the formula I mentioned in the preceding Examples, are prepared as follows:

Composition

| active ingredient | 1250 g |
| talc | 180 g |
| wheat starch | 120 g |
| magnesium stearate | 80 g |
| lactose | 20 g |

Preparation process: The substances mentioned are pulverized and forced through a sieve of 0.6 mm mesh size. 0.33 g portions of the mixture are dispensed into gelatin capsules using a capsule-filling machine.

EXAMPLE 41

Soft Capsules 5000 soft gelatin capsules, each comprising as active ingredient 0.05 g of one of the compounds of the formula I mentioned in the preceding Examples, are prepared as follows:

|  |  |
|---|---|
| active ingredient | 250 g |
| Lauroglycol | 2 liters |

Preparation process: The pulverized active ingredient is suspended in Lauroglycol® (propylene glycol laurate, Gattefossé S. A., Saint Priest, France) and ground in a wet pulverizer to a particle size of approx. 1 to 3 μm. 0.419 g portions of the mixture are then dispensed into soft gelatin capsules using a capsule-filling machine.

EXAMPLE 42

Soft Capsules 5000 soft gelatin capsules, each comprising as active ingredient 0.05 g of one of the compounds of the formula I mentioned in the preceding Examples, are prepared as follows:

Composition

|  |  |
|---|---|
| active ingredient | 250 g |
| PEG 400 | 1 liter |
| Tween 80 | 1 liter |

Preparation process: The pulverized active ingredient is suspended in PEG 400 (polyethylene glycol having an $M_r$ of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulverizer to a particle size of approx. 1 to 3 μm. 0.43 g portions of the mixture are then dispensed into soft gelatin capsules using a capsule-filling machine.

What is claimed is:
1. A compound of formula I

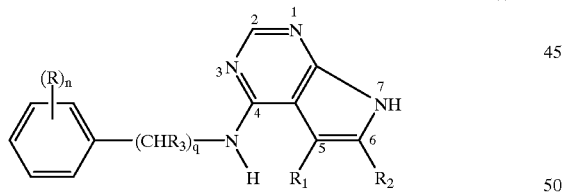

in which n is 0 to 3, q is 0 or 1,

R is halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, it being possible, if two or more radicals R are present in the molecule, for these to be identical to or different from one another, one of the radicals $R_1$ and $R_2$ is hydrogen or lower alkyl, and the other of the radicals $R_1$ and $R_2$ is a) a radical of the formula II

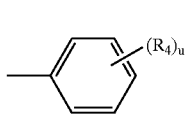

in which u is 1 to 3 and
one or more radicals $R_4$ is selected from the group consisting of amidino, guanidino, ureido, $N^3$-lower alkylureido, $N^3,N^3$-di-lower alkylureido, $N^3$-phenylureido, $N^3,N^3$-diphenylureido, thiocarbamoyl, thioureido, $N^3$-lower alkylthioureido, $N^3,N^3$-di-lower alkylthioureido, lower alkoxycarbonylamino, benzyloxycarbonylamino, morpholine-4-carbonyl, piperazine-1-carbonyl, 4-lower alkylpiperazine-1-carbonyl, lower alkylsulfonylamino, benzenesulfonylamino, toluenesulfonylamino, thiophene-2-carbonylamino, furan-2-carbonylamino, benzylamino, hydroxymethyl, aminomethyl or a radical of the formula —N=C($R_5$)—$R_6$, in which $R_5$ is hydrogen or lower alkyl and $R_6$ is di-lower alkylamino, piperidino, 4-lower alkylpiperazino or morpholino, and the other radical(s) $R_4$ is (are) halogen, lower alkyl, hydroxyl, lower alkanoyloxy, lower alkoxy, carboxyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, it being possible, if two or more radicals $R_4$ are present in the molecule, for these to be identical to or different from one another, or is b) a radical of the formula III

in which $R_7$ is lower alkoxy or benzyloxy and $R_8$ is hydroxyl or benzyloxy, or is c) amino-lower alkyl, in which the amino group is substituted by one or two hydroxy-lower alkyl, amino-lower alkyl, carboxy-lower alkyl, lower alkoxycarbonyl-lower alkyl, benzyloxycarbonyl-lower alkyl or benzyl radicals, which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or is d) piperidine-1-carbonyl, piperazine-1-carbonyl, 4-lower alkylpiperazine-1-carbonyl, morpholine-4-carbonyl, thiocarbamoyl, a heterocyclic radical bonded via a ring carbon atom and having five ring members and 1–4 ring heteroatoms, selected from oxygen, nitrogen and sulfur, or is e) 4-lower alkylpiperazinomethyl or a lower alkyl radical which is substituted by a heterocyclic radical other than piperazinyl and having five or six ring members and 1–4 ring heteroatoms, selected from oxygen, nitrogen and sulfur, or is f) a radical of the formula —CH═N—OR$_9$ in which R$_9$ is hydrogen or lower alkyl, or g) if q is 1, additionally to the definitions given above in the sections a) to f) can also be phenyl which is substituted by halogen, lower alkyl, trifluoromethyl or lower alkoxy, and R$_3$ is hydrogen, lower alkyl, lower alkoxycarbonyl, carbamoyl, N-lower alkylcarbamoyl or N,N-di-lower alkylcarbamoyl, or a salts thereof.

2. A compound of the formula I according to claim 1 in which

R$_1$ is hydrogen,

R$_2$ is pyrrolyl, thienyl, furyl, tetrazol-5-yl which is unsubstituted or substituted by lower alkyl or thiazol-2-yl which is unsubstituted or substituted by lower alkoxyphenyl, or methyl which is substituted by pyrrolyl, thienyl, furyl, morpholino, 4-lower alkylpiperazin-1-yl, tetrazol-5-yl which is unsubstituted or substituted by lower alkyl, or thiazol-2-yl which is unsubstituted or substituted by lower alkoxyphenyl, and the other radicals and symbols are as defined in claim 1, or a salt thereof.

3. A compound of the formula I according to claim 1 in which n is 0 or 1, q is 0 or 1, R is chlorine, R$_1$ is hydrogen, R$_2$ is a) a radical of the formula II

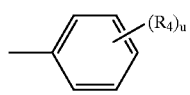

(II)

in which u is 1 and

R$_4$ is N$^3$-lower alkylureido, N$^3$-phenylureido, N$^3$-lower alkylthioureido, lower alkoxycarbonylamino, benzyloxycarbonylamino, morpholine-4-carbonyl, piperazine-1-carbonyl, 4-lower alkylpiperazine-1-carbonyl, lower alkylsulfonylamino, benzenesulfonylamino, toluenesulfonylamino, furan-2-carbonylamino, thiophene-2-carbonylamino, benzylamino, hydroxymethyl or a radical of the formula —N═C(R$_5$)—R$_6$ in which R$_5$ is hydrogen or lower alkyl and R$_6$ is di-lower alkylamino, piperidino, 4-lower alkylpiperazino or morpholino, or is b) a radical of the formula III

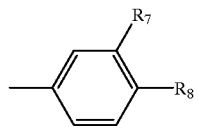

(III)

in which R$_7$ is lower alkoxy and R$_8$ is hydroxyl or benzyloxy, or is c) aminomethyl in which the amino group is substituted by one or two hydroxy-lower alkyl or benzyl radicals which in the phenyl moiety are unsubstituted or substituted by hydroxyl or lower alkoxy, or is d) piperazine-1-carbonyl, 4-lower alkylpiperazine-1-carbonyl, morpholine-4-carbonyl, thiocarbamoyl, thiazol-2-yl, 4-(4-methoxyphenyl)thiazol-2-yl, 4-ethylthiazol-2-yl, 4,5-dimethylthiazol-2-yl, tetrazol-5-yl, 2-methyltetrazol-5-yl or 1-methyltetrazol-5-yl, or is e) 4-lower alkylpiperazinomethyl or morpholinomethyl, or is f) a radical of the formula —CH═N—OR$_9$, in which R$_9$ is hydrogen or lower alkyl, or g) if q is 1, additionally to the definitions given above in sections a) to f) can also be phenyl which is substituted by lower alkoxy, and R$_3$ is hydrogen or lower alkyl, or a pharmaceutically acceptable salt thereof.

4. A compound of the formula I according to claim 1, selected from 4-(3-chloroanilino)-6-[(4-methylpiperazin-1-yl)methyl]-7H-pyrrolo[2,3-d]pyrimidine, 4-(3-chloroanilino)-6-(morpholin-4-yl)methyl]-7H-pyrrolo[2,3-d]pyrimidine, 4-(3-chloroanilino)-6-[bis(2-hydroxyethyl)aminomethyl)]-7H-pyrrolo[2,3-d]pyrimidine, 4-(3-chloroanilino)-6-[(4-methoxybenzylamino)methyl]-7H-pyrrolo[2,3-d]pyrimidine, 4-(3-chloroanilino)-6-[(4-hydroxybenzylamino)methyl]-7H-pyrrolo[2,3-d]pyrimidine, (E)-4-(3-chloroanilino)-7H-pyrrolo[2,3-d]pyrimidine-6-carbaldehyde oxime, (Z)-4-(3-chloroanilino)-7H-pyrrolo[2,3-d]pyrimidine-6-carbaldehyde oxime, 4-(3-chloroanilino)-7H-pyrrolo[2,3-d]pyrimidine-6-carbaldehyde O-methyoxime, 4-(3-chloroanilino)-6-(morpholin-4-yl-carbonyl)-7H-pyrrolo[2,3-d]pyrimidine, 4-(3-chloroanilino)-6-[(4-methylpiperazin-1-yl)carbonyl]-7H-pyrrolo[2,3-d]pyrimidine, 4-(3-chloroanilino)-6-(thiocarbamoyl)-7H-pyrrolo[2,3-d]pyrimidine, 4-(3-chloroanilino)-6-[4-(4-methoxyphenyl)thiazol-2-yl]-7H-pyrrolo[2,3-d]pyrimidine, 4-(3-chloroanilino)-6-(4-ethylthiazol-2-yl)-7H-pyrrolo[2,3-d]pyrimidine, 4-(3-chloroanilino)-6-(4,5-dimethylthiazol-2-yl)-7H-pyrrolo[2,3-d]pyrimidine, 4-(3-chloroanilino)-6-(tetrazol-5-yl)-7H-pyrrolo[2,3-d]pyrimidine, 4-(3-chloroanilino)-6-(2-methyltetrazol-5-yl)-7H-pyrrolo[2,3-d]pyrimidine, 4-(3-chloroanilino)-6-(1-methyltetrazol-5-yl)-7H-pyrrolo[2,3-d]pyrimidine,
(R)-6-(4-methylsulfonylaminophenyl)-4-[(1-phenylethyl)amino]-7H-pyrrolo[2,3-d]pyrimidine,
(R)-6-(4-ethylsulfonylaminophenyl)-4-[(1-phenylethyl)amino]-7H-pyrrolo[2,3-d]pyrimidine,
(R)-6-(4-isopropylsulfonylaminophenyl)-4-[(1-phenylethyl)amino]-7H-pyrrolo[2,3-d]pyrimidine,
(R)-6-(3-methylsulfonylaminophenyl)-4-[(1-phenylethyl)amino]-7H-pyrrolo[2,3-d]pyrimidine,
(R)-6-(3-ethylsulfonylaminophenyl)-4-[(1-phenylethyl)amino]-7H-pyrrolo[2,3-d]pyrimidine,
(R)-6-(3-isopropylsulfonylaminophenyl)-4-[(1-phenylethyl)amino]-7H-pyrrolo[2,3-d]pyrimidine,
6-(4-methylsulfonylaminophenyl)-4-(3-chloroanilino)-7H-pyrrolo[2,3-d]pyrimidine,
4-(3-chloroanilino)-6-(4-ethylsulfonylaminophenyl)-7H-pyrrolo[2,3-d]pyrimidine,
4-(3-chloroanilino)-6-(4-isopropylsulfonylaminophenyl)-7H-pyrrolo[2,3-d]pyrimidine,
4-(3-chloroanilino)-6-(4-phenylsulfonylaminophenyl)-7H-pyrrolo[2,3-d]pyrimidine,
4-(3-chloroanilino)-6-(3-methylsulfonylaminophenyl)-7H-pyrrolo[2,3-d]pyrimidine,
4-(3-chloroanilino)-6-(3-ethylsulfonylaminophenyl)-7H-pyrrolo[2,3-d]pyrimidine,
4-(3-chloroanilino)-6-(3-isopropylsulfonylaminophenyl)-7H-pyrrolo[2,3-d]pyrimidine,
4-(3-chloroanilino)-6-(4-[dimethylaminomethylenamino]phenyl)-7H-pyrrolo[2,3-d]pyrimidine,
4-(3-chloroanilino)-6-(4-[diethylaminomethylenamino]phenyl-7H-pyrrolo[2,3-d]pyrimidine,
4-(3-chloroanilino)-6-(4-[piperidinomethylenaminophenyl)-7H-pyrrolo[2,3-d]pyrimidine,
4-(3-chloroanilino)-6-(4-[morpholinomethylenamino]phenyl)-7H-pyrrolo[2,3-d]pyrimidine,
4-(3-chloroanilino)-6-{4-[(4-methylpiperazino)methylenamino]phenyl}-7H-pyrrolo[2,3-d]pyrimidine,
4-(3-chloroanilino)-6-(3-[dimethylaminomethylenamino]phenyl)-7H-pyrrolo[2,3-d]pyrimidine,
4-(3-chloroanilino)-6-(3-[diethylaminomethylenamino]phenyl)-7H-pyrrolo[2,3-d]pyrimidine,
4-(3-chloroanilino)-6-(3-[morpholinomethylenamino]phenyl)-7H-pyrrolo[2,3-d]pyrimidine,
(R)-6-(4-[dimethylaminomethylenamino]phenyl)-4-[(1-phenylethyl)amino]-7H-pyrrolo[2,3-d]pyrimidine,
(R)-6-(3-[dimethylaminomethylenamino]phenyl)-4-[(1-phenylethyl)amino]-7H-pyrrolo[2,3-d]pyrimidine,
4-(3-chloroanilino)-6-(4-[morpholin-4-ylcarbonyl]phenyl)-7H-pyrrolo[2,3-d]pyrimidine,
4-(3-chloroanilino)-6-(4-[4-methylpiperazin-1-ylcarbonyl]phenyl)-7H-pyrrolo[2,3-d]pyrimidine,
4-(3-chloroanilino)-6-(4-[$N^3$-ethylureido]phenyl)-7H-pyrrolo[2,3-d]pyrimidine,
4-(3-chloroanilino)-6-(3-[$N^3$-ethylureido]phenyl)-7H-pyrrolo[2,3-d]pyrimidine,
4-(3-chloroanilino)-6-(3-[$N^3$-phenylureidophenyl)-7H-pyrrolo[2,3-d]pyrimidine,
(R)-6-(4-[$N^3$-ethylureido]phenyl)-4-[(1-phenylethyl)amino]-7H-pyrrolo[2,3-d]pyrimidine,
(R)-6-(3-[$N^3$-ethylureido]phenyl)-4-[(1-phenylethyl)amino]-7H-pyrrolo[2,3-d]pyrimidine,
4-(3-chloroanilino)-6-(4-[$N^3$-methylthioureido]phenyl)-7H-pyrrolo[2,3-d]pyrimidine,
4-(3-chloroanilino)-6-(3-[$N^3$-methylthioureido]phenyl)-7H-pyrrolo[2,3-d]pyrimidine, (R)-6-(4-[$N^3$-methylthioureido]phenyl)-4-[(1-phenylethyl)amino]-7H-pyrrolo[2,3-d]pyrimidine,
(R)-6-(3-[$N^3$-methylthioureido]phenyl)-4-[(1-phenylethyl)amino]-7H-pyrrolo[2,3-d]pyrimidine,
4-(3-chloroanilino)-6-(4-methoxycarbonylaminophenyl)-7H-pyrrolo[2,3-d]pyrimidine,
4-(3-chloroanilino)-6-(4-ethoxycarbonylaminophenyl)-7H-pyrrolo[2,3-d]pyrimidine,
4-(3-chloroanilino)-6-(4-isopropyloxycarbonylaminophenyl)-7H-pyrrolo[2,3-d]pyrimidine,
4-(3-chloroanilino)-6-(4-[(2-methylpropyloxy)carbonylamino]phenyl)-7H-pyrrolo[2,3-d]pyrimidine,
(R)-6-(3-benzylaminophenyl)-4-[(1-phenylethyl)amino]-7H-pyrrolo[2,3-d]pyrimidine,
6-(4-benzyl oxy-3-m ethoxyphenyl)-4-(3-chloroanilino)-7H-pyrrolo[2,3-d]pyrimidine,
6-(4-benzyloxy-3-methoxyphenyl)-4-(3-methylanilino)-7H-pyrrolo[2,3-d]pyrimidine,
6-(4-hydroxy-3-methoxyphenyl)-4-(3-methylanilino)-7H-pyrrolo[2,3-d]pyrimidine,
4-anilino-6-(4-hydroxy-3-methoxyphenyl)-7H-pyrrolo[2,3-d]pyrimidine hydrochloride,
4-(3-chloroanilino)-6-(4-hydroxy-3-methoxyphenyl)-7H-pyrrolo[2,3-d]pyrimidine-hydrochloride,
4-(3-chloroanilino)-6-(4-[fur-2-ylcarbonylamino]phenyl)-7H-pyrrolo[2,3-d]pyrimidine,
4-(3-chloroanilino)-6-(4-[thien-2-ylcarbonylamino]phenyl)-7H-pyrrolo[2,3-d]pyrimidine,
6-(4-benzylaminophenyl)-4-(3-chloroanilino)-7H-pyrrolo[2,3-d]pyrimidine,
(R)-6-(4-methoxyphenyl)-4-[(1-phenylethyl)amino]-7H-pyrrolo[2,3-d]pyrimidine,
4-(3-chloroanilino)-6-(4-[(1-dimethylamino-1-isopropylmethylene)amino}phenyl)-7H-pyrrolo[2,3-d]pyrimidine and
4-(3-chloroanilino)-6-(thiazol-2-yl)-7H-pyrrolo[2,3-d]pyrimidine, or a pharmaceutically acceptable salt thereof.

5. A process for the preparation of a 7H-pyrrolo[2,3-d]pyrimidine derivative of the formula I

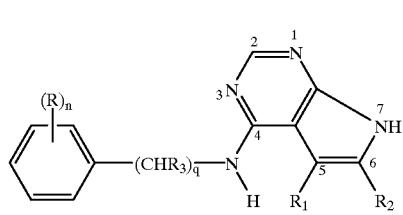

(I)

in which n is 0 to 3,
q is 0 or 1,
R is halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, it being possible, if two or more radicals R are present in the molecule, for these to be identical to or different from one another, one of the radicals $R_1$ and $R_2$ is hydrogen or lower alkyl, and the other of the radicals $R_1$ and $R_2$ is a) a radical of the formula II

in which u is 1 to 3 and at least one radical $R_4$ is amidino, guanidino, ureido, $N^3$-lower alkylureido, $N^3,N^3$-di-lower alkylureido, $N^3$-phenylureido, $N^3,N^3$-diphenylureido, thiocarbamoyl, thioureido, $N^3$-lower alkylthioureido, $N^3,N^3$-di-lower alkylthioureido, lower alkoxycarbonylamino, benzyloxycarbonylamino, morpholine-4-carbonyl, piperazine-1-carbonyl, 4-lower alkylpiperazine-1-carbonyl, lower alkylsulfonylamino, benzenesulfonylamino, toluenesulfonylamino, thiophene-2-carbonylamino, furan-2-carbonylamino, benzylamino, hydroxymethyl, aminomethyl or a radical of the formula —N=C($R_5$)—$R_6$, in which $R_5$ is hydrogen or lower alkyl and $R_6$ is di-lower alkylamino, piperidino, 4-lower alkylpiperazino or morpholino, and the other radical(s) $R_4$ is (are) halogen, lower alkyl, hydroxyl, lower alkanoyloxy, lower alkoxy, carboxyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, it being possible, if two or more radicals $R_4$ are present in the molecule, for these to be identical to or different from one another, or is b) a radical of the formula III

in which $R_7$ is lower alkoxy or benzyloxy and $R_8$ is hydroxyl or benzyloxy, or is c) amino-lower alkyl, in which the amino group is substituted by one or two hydroxy-lower alkyl, amino-lower alkyl, carboxy-lower alkyl, lower alkoxycarbonyl-lower alkyl, benzyloxycarbonyl-lower alkyl or benzyl radicals, which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or is d) piperidine-1-carbonyl, piperazine-1-carbonyl, 4-lower alkylpiperazine-1-carbonyl, morpholine-4-carbonyl, thiocarbamoyl, a heterocyclic radical bonded via a ring carbon atom and having five ring members and 1–4 ring heteroatoms, selected from oxygen, nitrogen and sulfur, or is e) 4-lower alkylpiperazinomethyl or a lower alkyl radical which is substituted by a heterocyclic radical other than piperazinyl and having five or six ring members and 1–4 ring heteroatoms, selected from oxygen, nitrogen and sulfur, or is f) a radical of the formula —CH=N—$OR_9$ in which $R_9$ is hydrogen or lower alkyl, or g) if q is 1, additionally to the definitions given above in the sections a) to f) can also be phenyl which is substituted by halogen, lower alkyl, trifluoromethyl or lower alkoxy, and $R_3$ is hydrogen, lower alkyl, lower alkoxycarbonyl, carbamoyl, N-lower alkylcarbamoyl or N,N-di-lower alkylcarbamoyl, or a salt thereof, which comprises a) reacting a pyrrolo[2,3-d]pyrimidine derivative of the formula IV

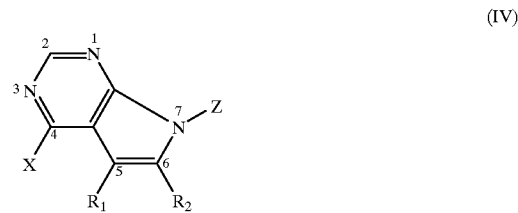

in which X is a suitable leaving group, Z is hydrogen or 1-aryl-lower alkyl and the other substituents are as defined above for compounds of the formula I, free functional groups present in the radicals $R_1$ and $R_2$ if necessary being protected by easily removable protective groups, with an aniline derivative of the formula V

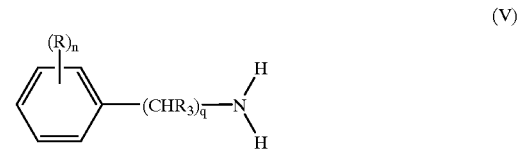

in which R, $R_3$, n and q are as defined above for compounds of the formula I, free functional groups present in the radical R if necessary being protected by easily removable protective groups, and removing protective groups present and, if present, the 1-aryl-lower alkyl radical Z, or b) reacting a pyrrolo[2,3-d]pyrimidin-4-one derivative of the formula VI

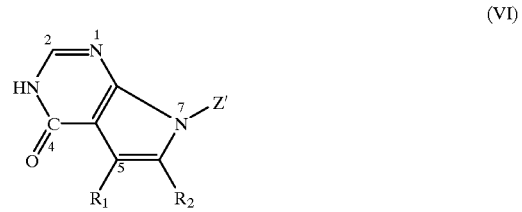

in which Z' is 1-aryl-lower alkyl and $R_1$ and $R_2$ are as defined above for compounds of the formula I, free functional groups present in the radicals $R_1$ and $R_2$ if necessary being protected by easily removable protective groups, in the presence of a dehydrating agent and a tertiary amine, with a phenylamine of the formula V above and removing protective groups present, or c) for the preparation of a compound of the formula I in which the radical R is hydroxyl or in which one of the radicals $R_1$ or $R_2$ is amino-lower alkyl in which the amino group is substituted by one or two benzyloxycarbonyl-lower alkyl or benzyl radicals which are substituted by hydroxyl in the phenyl moiety, and the other substituents are as defined above for compounds of the formula I, reacting a compound of the formula I in which the radical R is methoxy or in which one of the radicals $R_1$ or $R_2$ is amino-lower alkyl in which the amino group is substituted by one or two benzyloxycarbonyl-lower alkyl or benzyl radicals which are substituted by methoxy in the phenyl moiety, and the other substituents are as defined above for compounds of the formula I, free functional groups present in the radicals R, $R_1$ and $R_2$ if necessary being protected by easily removable protective groups, with boron tribromide, and removing protective groups present, or d) for the preparation of a compound of the formula I in which one of the radicals $R_1$ and $R_2$ is aminomethyl in which the amino group is substituted by one or two hydroxy-lower alkyl, amino-lower alkyl, carboxy-lower alkyl, lower alkoxycarbonyl-lower alkyl, benzyloxycarbonyl-lower alkyl or benzyl radicals which in the phenyl moiety are unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or in which one of the radicals $R_1$ and $R_2$ is 4-lower alkylpiperazinomethyl, morpholinomethyl or piperidinomethyl, and the other substituents are as defined above for compounds of the formula I, reacting a compound of the formula I in which one of the radicals $R_1$ and $R_2$ is formyl and the other substituents are as defined above for compounds of the formula I, free functional groups present in the radical R if necessary being protected by easily removable protective groups, with an amine of the formula VII

in which

α) $R_{10}$ is hydrogen, hydroxy-lower alkyl, amino-lower alkyl, carboxy-lower alkyl, lower alkoxycarbonyl-lower alkyl, benzyloxycarbonyl-lower alkyl or benzyl, the benzyloxycarbonyl-lower alkyl or benzyl radicals in the phenyl moiety being unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, and $R_{11}$ is hydroxy-lower alkyl, amino-lower alkyl, carboxy-lower alkyl, lower alkoxycarbonyl-lower alkyl, benzyloxycarbonyl-lower alkyl or benzyl, the benzyloxycarbonyl-lower alkyl or benzyl radicals in the phenyl moiety being unsubstituted or substituted by halogen, lower alkyl, hydroxymethyl, aminomethyl, hydroxyl, lower alkanoyloxy, lower alkoxy, carboxyl, lower alkanoyl, benzoyl, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl, or β) in which the radicals $R_{10}$ and $R_{11}$ together are pentane-1,5-diyl, 3-N-lower alkyl-3-azapentane-1,5-diyl or 3-oxapentane-1,5-diyl, catalytically hydrogenating the product and then removing protective groups present, or e) for the preparation of a compound of the formula I in which one of the radicals $R_1$ and $R_2$ is a radical of the formula —CH=N—$OR_9$ in which $R_9$ is hydrogen or lower alkyl, and the other substitutents are as defined above for compounds of the formula I, reacting a compound of the formula I, in which one of the radicals $R_1$ and $R_2$ is formyl and the other substituents are as defined above for compounds of the formula I, free functional groups present in the radical R if necessary being protected by easily removable protective groups, with a hydroxylamine derivative of the formula VIII

in which $R_{12}$ is hydrogen or lower alkyl, and removing protective groups present, or f) for the preparation of a compound of the formula I in which one of the radicals $R_1$ and $R_2$ is piperidine-1-carbonyl, piperazine-1-carbonyl, 4-lower alkylpiperazine-1-carbonyl or morpholine-4-carbonyl, and the other substituents are as defined above for compounds of the formula I, reacting a compound of the formula I in which one of the radicals $R_1$ and $R_2$ is carboxyl and the other substituents are as defined above for compounds of the formula I, free functional groups present in the radical R if necessary being protected by easily removable protective groups, or a reactive carboxylic acid derivative of such a compound, with an amine of the formula VII

in which the radicals $R_{10}$ and $R_{11}$ together are pentane-1,5-diyl, 3-azapentane-1,3-diyl, 3-N-lower alkyl-3-azapentane-1,3-diyl or 3-oxapentane-1,3-diyl, and then removing protective groups present, or g) for the preparation of a compound of the formula I in which one of the radicals $R_1$ and $R_2$ is thiocarbamoyl and the other substituents are as defined above for compounds of the formula I, reacting a compound of the formula I in which one of the radicals $R_1$ and $R_2$ is aminocarbonyl and the other substituents are as defined above for compounds of the formula I, free functional groups present in the radical R if necessary being protected by easily removable protective groups, with Lawesson's reagent, and then removing protective groups present, or h) for the preparation of a compound of the formula I in which one of the radicals $R_1$ and $R_2$ is $R_{13}$-thiazol-2-yl in which $R_{13}$ in each case is unsubstituted or substituted lower alkyl or phenyl and the other substituents are as defined above for compounds of the formula I, reacting a compound of the formula I in which one of the radicals $R_1$ and $R_2$ is thiocarbamoyl and the other substituents are as defined above for compounds of the formula I, free functional groups present in the radical R if necessary being protected by easily removable protective groups, with a compound of the formula IX

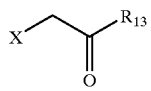

(IX)

in which X is a leaving group and $R_{13}$ in each case is unsubstituted or substituted lower alkyl or phenyl, free functional groups present in the radical $R_{13}$ if necessary being protected by easily removable protective groups, and then removing protective groups present, or i) for the preparation of a compound of the formula I in which one of the radicals $R_1$ and $R_2$ is tetrazol-5-yl and the other substituents are as defined above for compounds of the formula I, reacting a compound of the formula I in which one of the radicals $R_1$ and $R_2$ is cyano and other substituents are as defined above for compounds of the formula I, free functional groups present in the radical R if necessary being protected by easily removable protective groups, with a suitable alkali metal azide, and then removing protective groups present, or j) for the preparation of a compound of the formula I in which one of the radicals $R_1$ and $R_2$ is 2-lower alkyltetrazol-5-yl and the other substituents are as defined above for compounds of the formula I, reacting a compound of the formula I in which one of the radicals $R_1$ and $R_2$ is tetrazol-5-yl and the other substituents are as defined above for compounds of the formula I, free functional groups present in the radical R if necessary being protected by easily removable protective groups, with the appropriate lower alkyl iodide, and then removing protective groups present, or k) for the preparation of a compound of the formula I in which one of the radicals $R_1$ and $R_2$ is a radical of the formula II

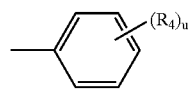

(II)

in which at least one radical $R_4$ is lower alkylsulfonylamino, benzenesulfonylamino or toluenesulfonylamino, and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with a compound of the formula X

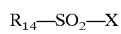 $R_{14}$—$SO_2$—X (X)

in which X is chlorine or bromine and $R_{14}$ is lower alkyl, phenyl or 4-methylphenyl, and then removing protective groups present, or l) for the preparation of a compound of the formula I in which one of the radicals $R_1$ and $R_2$ is a radical of the formula II

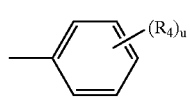

(II)

in which at least one radical $R_4$ is a radical of the formula —N=C($R_5$)—$R_6$ in which $R_5$ is hydrogen and $R_6$ is as defined above for compounds of the formula I and the other substituents and symbols are as defined above for compounds of the formula I, reacting a compound of the formula I in which one of the radicals $R_1$ and $R_2$ is a radical of the formula II in which at least one radical $R_4$ is amino and other substituents and symbols are as defined above for compounds of the formula I, free functional groups present in the radical R and, if present, the other radicals $R_4$ if necessary being protected by easily removable protective groups, with an acetal of the formula XI

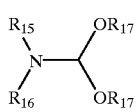

(XI)

in which $R_{15}$ and $R_{16}$ are each individually lower alkyl or together are pentane-1,5-diyl, 3-N-lower alkyl-3-azapentane-1,5-diyl or 3-oxapentane-1,5-diyl, and each $R_{17}$ is lower alkyl, and then removing protective groups present, or m) for the preparation of a compound of the formula I in which one of the radicals $R_1$ and $R_2$ is a radical of the formula II

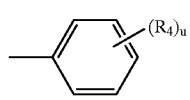

(II)

in which at least one radical $R_4$ is $N^3$-lower alkylureido or $N^3$-phenylureido and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with an isocyanate of the formula XII

 $R_{18}$—N=C=O (XII)

in which $R_{18}$ is lower alkyl or phenyl, and then removing protective groups present, or n) for the preparation of a compound of the formula I in which one of the radicals $R_1$ and $R_2$ is a radical of the formula II

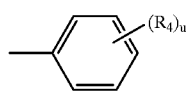

(II)

in which at least one radical $R_4$ is $N^3$-lower alkylthioureido or $N^3$-phenylthioureido and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with an isothiocyanate of the formula XIII

 (XIII)

in which $R_{18}$ is lower alkyl or phenyl, and then removing protective groups present, or o) for the preparation of a compound of the formula I in which one of the radicals $R_1$ and $R_2$ is a radical of the formula II

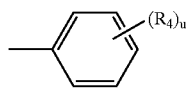

(II)

in which at least one radical $R_4$ is lower alkoxycarbonylamino or benzyloxycarbonylamino and the other substituents and symbols are as defined above for compounds of the formula I, reacting a compound of the formula I in which one of the radicals $R_1$ and $R_2$ is a radical of the formula II in which at least one radical $R_4$ is amino and the other substituents and symbols are as defined above for compounds of the formula I, free functional groups present in the radical R and, if present, the other radicals $R_4$ if necessary being protected by easily removable protective groups, with a chloroformic acid ester of the formula XIV

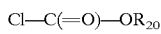 (XIV)

in which $R_{20}$ is lower alkyl or benzyl, and then removing protective groups present, and after carrying out one of the process variants a) to o), if necessary for the preparation of a salt, converting a free compound of the formula I obtained into a salt or, if necessary for the preparation of a free compound, converting a salt of a compound of the formula I obtained into the free compound.

6. A pharmaceutical composition comprising a pharmaceutically acceptable carrier or diluent and a therapeutically effective amount of a compound of formula I according to claim 1, or a pharmaceutically acceptable salt thereof.

7. A method of treating tumors which are responsive to an inhibition of the tyrosine kinase activity of the receptor for EGF comprising administering to a warm-blooded animal in need of such treatment a therapeutically effective amount of a compound of formula I according to claim 1, or a pharmaceutically acceptable salt thereof.

8. A method of claim 7 wherein the warm-blooded animal is a human.

* * * * *